United States Patent [19]

Sugihara et al.

[11] Patent Number: 5,294,713
[45] Date of Patent: Mar. 15, 1994

[54] 2-PIPERAZINONE COMPOUNDS AND THEIR USE

[75] Inventors: Hirosada Sugihara, Mishima; Zenichi Terashita, Suita, both of Japan

[73] Assignee: Takeda Chemical Industries, Ltd., Osaka, Japan

[21] Appl. No.: 926,171

[22] Filed: Aug. 7, 1992

[30] Foreign Application Priority Data

Aug. 23, 1991 [JP] Japan .................... 2-212397
May 15, 1992 [JP] Japan .................... 3-123146

[51] Int. Cl.$^5$ .................... C07D 241/04
[52] U.S. Cl. .................... 544/384
[58] Field of Search .................... 544/384

[56] References Cited

FOREIGN PATENT DOCUMENTS 2008311 7/1990 Canada .
0483667 5/1992 European Pat. Off. .

Primary Examiner—Frederick E. Waddell
Assistant Examiner—William R. A. Jarvis
Attorney, Agent, or Firm—Wegner, Cantor, Mueller & Player

[57] ABSTRACT

The compounds of the formula

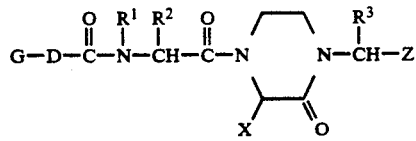

wherein G stands for an amidino group or an optionally cyclic amino group, these being respectively optionally substituted; D stands for a spacer having 2 to 6 atomic chain optionally bonded through a hetero-atom and/or a 5- to 6-membered ring (provided that the 5- to 6-membered ring is, depending on its bonding position, counted as 2 to 3 atomic chains); $R^1$ stands for hydrogen, benzyl group or a lower alkyl group; $R^2$ and $R^3$ independently stand for a residual group formed by removing $-CH(NH_2)COOH$ from an α-amino acid, or $R^1$ and $R^2$ may form a 5- to 6-membered ring taken together with the adjacent N and C; X stands for hydrogen or an optionally substituted lower alkyl group; and Z stands for a group capable of forming an anion or a group convertible into an anion in a living body, or salts thereof and agents for inhibiting cell-adhesion, which are characterized by containing these compounds. The novel compounds and pharmaceutical agents are effective for prophylaxis and therapy of various diseases by controlling or inhibiting cell adhesion.

25 Claims, No Drawings

2-PIPERAZINONE COMPOUNDS AND THEIR USE

This invention relates to novel 2-piperazinone compounds or salts thereof and agents for inhibiting adhesion of animal cells containing said compounds as their effective component.

The present invention also provides methods for producing said 2-piperazinone compounds. As the factors participating in adhesion to extracellular matrix of animal cells, there have been known fibronectin, vitronectin, osteopontin, collagens, thrombospondin, fibrinogen and von Willebrand factor. These proteins include —Arg—Gly—Asp— as cell recognition site. This tripeptide is recognized by at least one member of a family of receptors, integrin, which are heterodimeric proteins with two membrane-spanning subunits. (E. Ruoslahti and M. D. Pierschbacher, *Science*, 238, 491 (1978)).

Structurally related receptors, integrins, which recognize the amino acid sequence —Arg—Gly—Asp—, are known to express at extracellular surface glycoprotein, GP IIb/IIIa of platelets, endothelial cells, leucocyte, lymphocyte, monocyte and granulocyte. Compounds having the amino acid sequence —Arg—Gly—Asp— are competitively bound to the site to be bound with intracellular adhesive factors to thereby inhibit the binding of intracellular adhesive factors. As such intracellular adhesive factors, for example, H—Gly—Arg—Gly—Asp—Ser—Pro—OH has been known.

When blood vessels are injured, platelets are activated with, for example, endothelial collagens, which causes binding of fibrinogen to platelets, i.e. platelet aggregation, to form thrombus. The interaction between blood platelets and fibrinogen takes place through GP IIb/IIIa, this being an important characteristic feature of platelet aggregation. Cell adhesion-inhibiting substances can inhibit platelet aggregation due to substances causing blood platelet aggregation, e.g. thrombin, epinephrine, ADP or collagen.

Besides, cell-adhesion inhibiting substances are expected as drugs for suppression of metastasis of tumor cells (inhibition of fixed adhesion at the site where the tumor cells are migrated).

Linear or cyclic peptides containing the amino acid sequence, —Arg—Gly—Asp— have been known as cell-adhesion inhibiting substances, in, for example, the *Journal of Biological Chemistry*, 262, 17294 (1987) and European Patent Application No. 89910207.

These peptide derivatives are not satisfactory in the potency of their activity, and their oral absorbability is not satisfactory. Since these peptide derivatives are hydrolyzed with enzymes including aminopeptidase, carboxypeptidase or various endopeptidases, e.g. serine-protease, their stability in a solution containing these enzymes or in a living body is not satisfactory. Therefore, for clinical application of these peptide derivatives, there are problems still to be solved.

The present invention relates to novel 2-piperazinone compounds free from the above problems, and to drugs performing cell adhesion-inhibiting effects comprising these derivatives as effective components.

More specifically, the present invention relates to the compounds represented by the formula

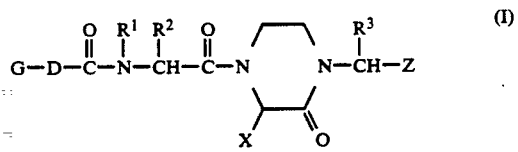

wherein G stands for an amidino group or an optionally cyclic amino group each of which may be substituted; D stands for a spacer having a 2 to 6 atomic chain optionally bonded through a hetero-atom and/or a 5- to 6-membered ring provided that the 5- to 6-membered ring is, depending on its bonding position, counted as 2 to 3 atomic chains; $R^1$ stands for hydrogen, benzyl group or a lower alkyl group; $R^2$ and $R^3$ independently stand for a residual group formed by removing —CH(NH$_2$)COOH from an α-amino acid, or $R^1$ and $R^2$ may form a 5- to 6-membered ring taken together with the adjacent N and C; X stands for hydrogen or an optionally substituted lower alkyl group; and Z stands for a group capable of forming an anion or a group convertible into an anion in a living body, or physiologically acceptable salts thereof, among others, especially to the compounds of the formula

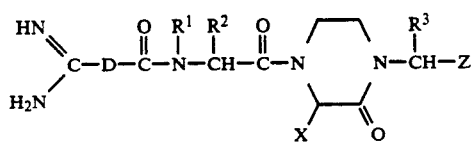

wherein D stands for a spacer having 3 to 6 atomic chain optionally bonded through a hetero-atom and/or a 5- to 6-membered ring provided that the 5- to 6-membered ring is, depending on its bonding position, counted as 2 to 3 atomic chain; $R^1$ stands for hydrogen, benzyl group or a lower alkyl group; $R^2$ and $R^3$ stand for a residual group formed by removing —CH(NH$_2$)COOH from an α-amino acid; X stands for hydrogen or a lower alkyl group optionally substituted with a substituent selected from the group consisting of (1) an optionally esterified or amidated carboxyl group, (2) an optionally substituted phenyl group and (3) hydroxyl group; and Z stands for an optionally esterified or amidated carboxyl group, or salts thereof, and to agents for inhibiting cell-adhesion, which are characterized by containing a compound described above.

Furthermore, the present invention is to provide a method of preparing the novel compounds represented by the formula (I) and salts thereof.

Examples of the optionally cyclic amino group which may be substituted, as represented by G, include acyclic primary amino groups or acyclic or cyclic secondary or tertiary amino groups substituted with a C$_{1-4}$ alkyl group or having a protective group capable of functioning physiologically.

Examples of the amino-protective group capable of functioning physiologically include lower (C$_{2-5}$) alkanoyl groups such as acetyl, propionyl and butyryl, optionally substituted benzoyl groups such as benzoyl and 3,4,5-trimethoxybenzoyl, acyl groups derived from an α-amino acid such as L-alanyl, L-phenylalanyl and L-leucyl, namely, a residual group formed by removing OH of —COOH from alpha-amino acid, lower (C$_{2-5}$) alkoxycarbonyl groups such as methoxycarbonyl and ethoxycarbonyl, optionally substituted phenoxycarbonyl groups, optionally substituted $C_{8-14}$ aralkyloxycarbonyl groups such as benzyloxycarbonyl and p-methoxybenzyloxycarbonyl.

In the formula (I), G may be such a cyclic secondary amino group as shown by

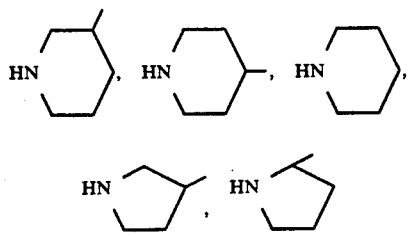

or such a tertiary amino group as shown by

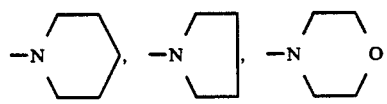

Preferable substituents of the optionally substituted amidino groups include $C_{1-4}$ alkyl groups.

Especially preferably groups of G are unsubstituted amidino groups and unsubstituted amino group.

Examples of the hetero-atoms in the spacer having 2 to 6 atomic chains optionally bonded through a 5- to 6-membered ring and/or hetero-atoms, as represented by D in the above formula (I), include atoms of N, O and S. The 5- to 6-membered rings may be a carbocyclic ring or a heterocyclic ring having 1 to 4 hetero-atoms selected from N, O and S, and they may be a saturated ring or unsaturated ring such as aromatic rings. Examples of these 5- to 6-membered rings include the following

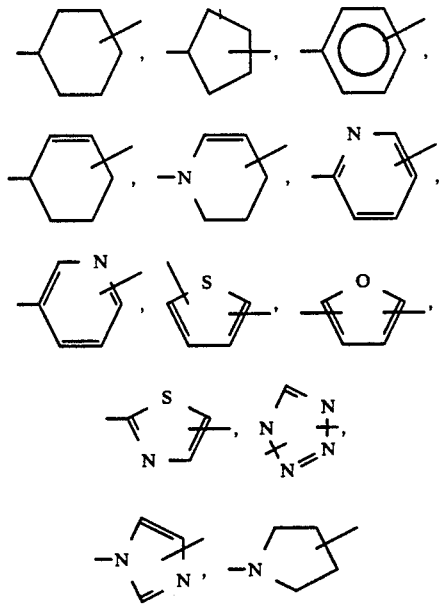

The above-mentioned 5- to 6-membered rings are preferably those not having a bond at the adjacent sites on the ring. While it is preferable that the above-mentioned 5- to 6-membered rings have bonds at the second to third sites on the ring counted from each other, these rings, either saturated or unsaturated, are usually regarded at 2 to 3 atomic chain, and groups of 2 to 6 atomic chain are preferable as D itself. As the hetero-atoms existing in the spacer shown by D, nitrogen is especially preferable. More specifically, D bonding to the adjacent G such as amidino group through —NH— group is preferable. The above-mentioned 5- to 6-membered ring may be bonded to the adjacent G such as amidino group directly, through —NH— group, or through a methylene chain. The above-mentioned 5- to 6-membered ring in D may be bonded to the adjacent carbonyl group, directly, through a methylene chain or through hetero-atoms.

The methylene chain in D is optionally substituted with a group represented by the formula

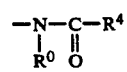

wherein $R^0$ stands for hydrogen or a lower alkyl group optionally substituted with an optionally substituted phenyl group; $R^4$ stands for a lower alkyl group optionally substituted with an optionally substituted phenyl group or an optionally substituted phenyl group or benzyloxy group. Thus, as typical groups represented by D, those represented by the formula

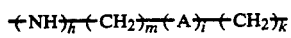

wherein h and i respectively denote 0 or 1; m and k respectively denote 0, 1 or 2; A stands for preferably a 5- to 6-membered ring, especially cyclohexane ring, benzene ring, piperidine or a group represented by the formula

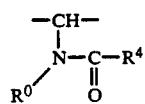

(hereinafter referred to as formula $D_1$) are preferable. Especially, as A, 5- to 6-membered rings (hereinafter referred to as $A_1$) are preferable. Preferably, h denotes 0 or 1, m denotes preferably 0 or 1 and k denotes preferably 0. Among the 5- to 6-membered rings represented by $A_1$, benzene ring and cyclohexane ring are desirable, and further, benzene ring is especially preferable.

In the above-mentioned formula (I), groups represented by the formula

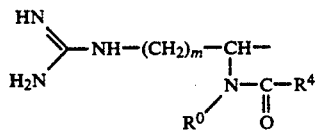

wherein $R^0$, $R^4$ and m are of the same meaning as defined in the foregoing are substituents derived from arginine or homoarginine.

As D, groups represented by the formula

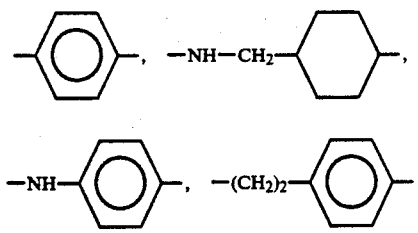

are especially preferable.

Lower alkyl groups of the optionally substituted lower alkyl groups represented by $R^0$, $R^4$ and $R^1$ and X as well as lower alkyl groups as the substituents of the substituted amidino group or amino group represented by G include $C_{1-4}$ alkyl groups such as methyl, ethyl, propyl, isopropyl, n-butyl and sec-butyl. Typical examples of the substituents of the substituted lower alkyl groups represented by X include optionally esterified or amidated carboxyl groups, optionally substituted phenyl groups, 5- to 6-membered heterocyclic groups and hydroxyl group. Examples of the substituents on the benzene ring of the lower alkyl groups which may be substituted with an optionally substituted phenyl group represented by $R^0$, $R^4$ or X, and the substituents on the benzene ring of the optionally substituted phenyl group represented by $R^4$ include lower ($C_{1-4}$) alkyl groups (e.g. methyl, ethyl, propyl, isopropyl, n-butyl, sec-butyl group), lower ($C_{1-4}$) alkoxy groups (e.g. methoxy, ethoxy group), halogen (e.g. chlorine, fluorine, bromine) and hydroxyl group.

As the 5- to 6-membered heterocyclic ring as the substituent of the optionally substituted lower alkyl group represented by X, saturated or unsaturated rings may be mentioned so long as they are 5- to 6-membered rings containing 1 to 4 hetero-atoms such as N, S and O, as preferably exemplified by benzene ring, pyridine ring, imidazole ring, thiophene ring, tetrazole ring and oxadiazole ring.

As groups represented by $R^2$ and $R^3$, any one can be mentioned so long as it is a residual group formed by removing —CH(NH$_2$)COOH from an α-amino acid. $R^1$ and $R^2$ may form a 5- to 6-membered ring taken together with the adjacent N and C. As such 5- to 6-membered rings, those shown by the formula

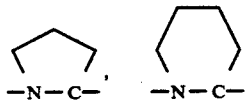

are preferable.

As $R^2$ and $R^3$, residues of essential amino acids are generally preferable. As $R^2$ and $R^3$, among others, preferred are hydrogen, $C_{1-4}$ lower alkyl groups, $C_{1-4}$ lower alkyl groups substituted with an optionally substituted phenyl as mentioned for X, $C_{1-4}$ lower alkyl groups substituted with hydroxy group, $C_{1-4}$ lower alkyl groups substituted with carbamoyl group, etc. More specifically, hydrogen, methyl, isopropyl, sec-butyl, isobutyl, hydroxymethyl, benzyl, p-hydroxybenzyl, p-methoxybenzyl, carbamoyl methyl and carbamoyl ethyl are mentioned as typical examples.

Among the compounds represented by the formula (I), those wherein each of $R^1$, $R^2$ and $R^3$ is hydrogen atom are preferable.

Examples of the group capable of forming an anion or the group capable of converting thereinto in a living body, which is represented by Z, include optionally esterified or amidated carbonyl groups or 5- to 6-membered heterocyclic groups which are acidic groups similar to carboxyl group. Preferable examples of these acidic 5- to 6-membered heterocyclic groups include heterocyclic groups usually bonded through their carbon atoms, such as tetrazol-5-yl and 5-oxo-2,5-dihydro-1,2,4-oxadiazol-3-yl. In the above-mentioned formula, the optionally esterified or amidated carboxyl group represented by Z and the esterified or amidated carboxyl group as the substituent of the lower alkyl group represented by X are respectively shown by the formulae

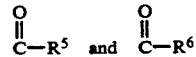

respectively.

In general, $R^5$ and $R^6$ independently stand for hydroxyl group, a $C_{1-8}$ alkoxy group (e.g. methoxy, ethoxy, propoxy, butoxy), a $C_{3-12}$ alkenyloxy group such as allyloxy or butenyloxy, or an aralkyloxy group (e.g. a phenyl lower alkyloxy group whose lower alkyl portion has a carbon number of about 1 to 4, such as benzyloxy, phenethyloxy or 3-phenylpropyloxy) or respectively stand for an optionally substituted amino group represented by —NR$^7$R$^8$ or —NR$^9$R$^{10}$. In NR$^7$R$^8$ and NR$^9$R$^{10}$, R$^7$ and R$^8$, R$^9$ and R$^{10}$ independently stand for hydrogen, a lower alkyl group (a $C_{1-6}$ lower alkyl group such as methyl, ethyl, propyl, butyl or hexyl), a $C_{3-8}$ alkenyl group (e.g. allyl, 2-butenyl, 3-pentenyl ) or a $C_{6-12}$ aralkyl group (e.g. benzyl, phenethyl, phenyl, propyl, pyridylmethyl) in which the aryl group may be unsubstituted or substituted with one or two substituents as exemplified by nitro, halogen (chlorine, fluorine, bromine), a lower ($C_{1-4}$) alkyl group (methyl, ethyl, propyl), or a lower ($C_{1-4}$) alkoxy group (methoxy, ethoxy, propoxy).

More specifically stating, in the case of formulating the compound (I) into an orally administrable preparation of a prodrug type, it is preferable to introduce, as the above-mentioned $R^5$ and $R^6$, a hydroxyl group, an optionally substituted amino [e.g. amino, an N-lower ($C_{1-4}$) alkylamino or an N,N-dilower ($C_{1-4}$) alkylamino] or an optionally substituted alkoxy [e.g. a lower ($C_{1-6}$) alkoxy whose alkyl moiety is optionally substituted by hydroxy or an optionally substituted amino (e.g. amino, dimethylamino, diethylamino, piperidino or morpholino), halogen, a lower ($C_{1-6}$) alkoxy, a lower ($C_{1-6}$) alkylthio, or an optionally substituted dioxolenyl (e.g. 5-methyl-2-oxo-1,3-dioxolenyl)] or a group represented by the formula of —OCH(R$^{11}$)OCOR$^{12}$ [wherein R$^{11}$ stands for hydrogen, a $C_{1-6}$ straight-chain or branched lower alkyl group (e.g. methyl, ethyl, n-propyl, isopropyl, n-butyl, isobutyl, t-butyl, n-pentyl, isopentyl, and neopentyl), a $C_{5-7}$ cycloalkyl (e.g. cyclopentyl, cyclohexyl or cycloheptyl), and R$^{12}$ stands for a $C_{1-6}$ straight-chain or branched lower alkyl group (e.g. methyl, ethyl, n-propyl, isopropyl, n-butyl, isobutyl, sec-butyl, t-butyl, n-pentyl, isopentyl, neopentyl), a $C_{2-8}$ lower alkenyl group (e.g. vinyl, propenyl, allyl, isopropenyl), a $C_{5-7}$ cycloalkyl group (e.g. cyclopentyl, cyclohexyl, cycloheptyl), a $C_{1-3}$ lower alkyl substituted with a $C_{5-7}$ cycloalkyl such as cyclopentyl, cyclohexyl, cycloheptyl or an aryl group such as phenyl group (e.g. benzyl, p-chlorobenzyl, phenethyl, cyclopentylmethyl, cyclohexylmethyl), a $C_{2-3}$ lower alkenyl group substituted with a $C_{5-7}$ cycloalkyl (e.g. cyclopentyl, cyclohexyl, cycloheptyl) or an aryl group such as phenyl group [groups having alkenyl moiety such as vinyl, propenyl, allyl, isopropenyl (e.g. cinnamyl)], an aryl group such as an optionally substituted phenyl group (e.g. phenyl, p-tolyl, naphthyl), a $C_{1-6}$ straight-chain or branched lower alkoxy group (e.g. methoxy, ethoxy, n-propoxy, isopropoxy, n-butoxy, isobutoxy, sec-butoxy, t-butoxy, n-pentyloxy, isopentyloxy, neopentyloxy), a $C_{2-8}$ straight-chain or branched lower alkenyloxy group (e.g. allyloxy, isobutenyloxy), a $C_{5-7}$ cycloalkyloxy group (e.g. cyclopentyloxy), a $C_{1-3}$ lower alkoxy group substituted with a $C_{5-7}$ cycloalkyl (e.g. cyclopentyl, cyclohexyl, cycloheptyl) or an aryl group (e.g. an optionally substituted phenyl) [groups having alkoxy moiety such as methoxy, ethoxy, n-propoxy, isopropoxy (e.g. benzyloxy, phenethyloxy, cyclopentylmethyloxy, cyclohexylmethyloxy)], a $C_{2-3}$ lower alkenyloxy group substituted with a $C_{5-7}$ cycloalkyl (e.g. cyclopentyl, cyclohexyl, cycloheptyl) or with an aryl group optionally substituted phenyl) [groups having alkenyloxy moiety such as vinyloxy (e.g. cinnamyloxy), propenyloxy, allyloxy, isopropenyloxy)] or an aryloxy group such as an optionally substituted phenoxy group (e.g. phenoxy, p-nitrophenoxy, naphthoxy)].

Especially in the case of using a prodrug, preferable examples of the esterified carboxyl groups represented by Z and the esterified carboxyl groups as the substituent of the optionally substituted lower alkyl group represented by X include —COOMe, —COOEt, —COOtBu, —COOPr, pivaloylomethoxycarbonyl, 1-(cyclohexyloxycarbonyloxy)ethoxycarbonyl, 5-methyl-2-oxo-1,3-dixolen-4-ylmethoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, and cyclopentylcarbonyloxymethoxycarbonyl.

As X, among others, preferred are hydrogen, benzyl, —CH$_2$COOH, —CH$_2$COOCH$_3$, —CH$_2$CONH$_2$, —CH$_2$CH$_2$COOH, —CH$_2$CH$_2$COOCH$_3$, —CH$_2$CH$_2$CONH$_2$, etc., and as Z, —COOH is preferable The compound (I) of this invention has one or more asymmetric carbons in the molecule, and both R-configurated ones and S-configurated ones are included in the present invention.

The compound (I) may be hydrated, and the compound (I) and its hydrate are hereinafter referred to the compound (I) inclusively.

When the salts of the compound (I) are used for a cell adhesion-inhibiting agent, physiologically acceptable salts thereof are desirable.

Examples of such physiologically acceptable salts of the compound (I) include inorganic acid salts such as hydrochloride, hydrobromide, sulfate, nitrate and phosphate, organic acid salts such as acetate, tartrate, citrate, fumarate, maleate, toluenesulfonate and methanesulfonate, metal salts such as sodium salt, potassium salt, calcium salt and aluminum salt, and salts with a base such as triethylamine salt, guanidine salt, ammonium salt, hydrazine salt, quinine salt and cinchonine salt.

Preferred compounds of the formula (I) are those in which G is unsubstituted amidino group and unsubstituted amino group, D is a preferable group as described above, especially a group of the formula

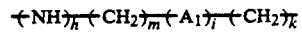

(wherein the symbols are of the same meaning as described above), R$^1$ is hydrogen, R$^2$ and R$^3$ are hydrogen, X is a lower alkyl group, among others, methyl or ethyl group, which may be substituted with benzyl, carboxyl group, an esterified carboxyl (particularly methyl ester), or an amidated carboxyl, and Z is carboxyl group or a group convertible into carboxyl group in a living body.

Specific examples of preferable compounds include
(S)-4-(trans-4-guanidinomethylcyclohexylcarbonylglycyl)-2-oxopiperazine-1,3-diacetic acid hydrochloride,
(S)-4-(4-guanidinomethylbenzoylglycyl)-2-oxopiperazine-1,3-diacetic acid hydrochloride,
(S)-4-(4-guanidinobenzoylsarcosyl)-2-oxopiperazine-1,3-diacetic acid hydrochloride,
(S)-4-(4-guanidinomethylbenzoylsarcosyl)-2-oxopiperazine-1,3-diacetic acid hydrochloride,
(S)-4-(4-guanidinomethylbenzoylsarcosyl)-2oxopiperazine1,3-diacetic acid hydrochloride,
(S)-1-carboxymethyl-4-(4-guanidinobenzoylsarcosyl)-2-oxopiperazine-3-propionic acid hydrochloride,
(S)-4-(3-guanidinophenylacetylglycyl)-2-oxopiperazine-1,3-diacetic acid hydrochloride,
(S)-4-(4-amidinobenzoylglycyl)-2-oxopiperazine-1,3-diacetic acid,
(S)-4-[4-(2-aminoethyl)benzoylglycyl]-2-oxopiperazine-1,3-diacetic acid,
4-(4-amindinobenzoylglycyl)-2-oxopiperazine-1-acetic acid,
(S)-4-(4-amidinobenzoylglycyl)-3-methoxycarbonylmethyl-2-oxopiperazine-1-acetic acid,
(S)-4[4-(2-aminoethyl)benzoylglycyl]-3-methoxycarbonylmethyl-2-oxopiperazine-1-acetic acid,
(S)-4-(4-amidinobenzoylglycyl)-3-benzyl-2-oxopiperazine-1-acetic acid,
(S)-4-(4-amidinobenzoylglycyl)-3-carbamoylmethyl-2-oxopiperazine-1-acetic acid,
(S)-4-(4-amidinobenzoylglycyl)-1-carboxymethyl-2-oxopiperazine-3-propionic acid,
(S)-4-[4-(2-aminoethyl)benzoylglycyl]-1-carboxymethyl-2-oxopiperazine-3-propionic acid,
(S)-4-[4-(2-aminoethyl)benzoylglycyl]-1-carboxymethyl-2-oxopiperazine-1-acetic acid,
(S)-4-[4-(2-aminoethyl)benzoylglycyl]-3-carbamoylmethyl-2-oxopiperazine-1-acetic acid,
(S)-4-[4-(2-aminoethyl)benzoylglycyl]-3-methoxycarbonylmethyl-2-oxopiperazine-1-acetic acid,
(S)-4-[4-(2-aminoethyl)benzoylglycyl]-3-methoxycarbonylmethyl-2-oxopiperazine-1-acetic acid,
(S)-4-[4-(2-aminoethyl)benzoylglycyl]-3-carbamoylethyl-2-oxopiperazine-1-acetic acid and their hydrochlorides.

The compound (I) of this invention can be produced by, for example, methods as described below. In the following description of the production methods, when R$^2$, R$^3$ in the starting compound contain functional groups (especially carboxyl group and amino group) and when X in the starting compound contains similarly carboxyl group, these functional groups may, upon necessity, be protected with a protective group conventionally used in the field of peptides, and in the following description, $R^2$, $R^3$ and X include these protected groups as well. Needless to state, introduction of protective groups into these functional groups and elimination thereof can be conducted in accordance with conventional means.

The compound (I) can be produced by a) subjecting a compound represented by the formula

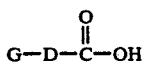
(II)

wherein symbols are of the same meaning as defined above and a compound represented by the formula

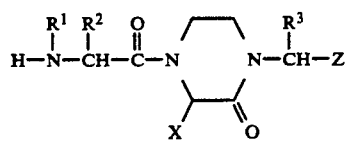
(III)

wherein symbols are of the same meaning as defined above, to condensation, or b) subjecting a compound represented by the formula

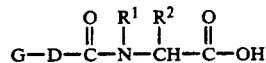
(IV)

wherein symbols are of the same meaning as defined above and a compound represented by the formula

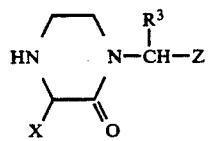
(V)

wherein symbols are of the same meaning as defined above, to condensation, or c) converting the cyano group in a compound represented by the formula

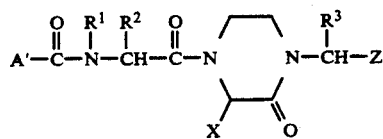
(VI)

wherein A, stands for $NC-(CH_2)_m-(A_1)_l-(CH_2)_k$ (wherein symbols are of the same meaning as defined above), into an amidino group or reducing the cyano group into an amino group, or d) converting the amino group in a compound represented by the formula

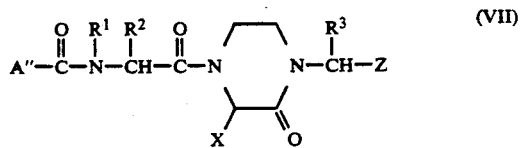
(VII)

wherein A" stands for $H_2N-(CH_2)_m-(A_1)_l-(CH_2)_k$ (wherein each symbol is of the same meaning as defined above), into a guanidino group.

The condensation reaction in the above methods a) and b) can be conducted by an amido-linkage formation reaction in a conventional peptide synthesis, for example, the method using active ester, mixed acid anhydride or acid chloride. For example, the condensation reaction between the compound (II) and the compound (III) or the compound (IV) and the compound (V) can be conducted by subjecting the compound (II) or the compound (IV) to condensation with a phenol such as 2,4,5-trichlorophenol, pentachlorophenol, 2-nitrophenol or 4-nitrophenol or an N-hydroxy compound such as N-hydroxysuccinimide, N-hydroxy-5-norbornen-endo-2,3-dicarboximide (HONB), 1-hydroxybenztriazole (HOBT) or N-hydroxypiperidine in the presence of a catalyst such as dicyclohexylcarbodiimide to convert into an active ester thereof, followed by condensation. Alternatively, the compound (II) or the compound (IV) is allowed to react with isobutyl chloroformate to give a mixed acid anhydride, which is then subjected to condensation.

The condensation between the compound (II) and the compound (III) or the compound (IV) and the compound (V) can be performed by using singly a reagent for peptide-formation such as dicyclohexylcarbodiimide, N,N,-carbonyldimidazole, diphenylphosphoryl azide or diethyl cyanophosphonate.

In said condensation reaction, the amidino group or the guanidino group present in the formula of the compound (II) or the compound (IV) is preferably present as the salt of an inorganic acid (e.g. hydrochloride, sulfate, nitrate, hydrobromide) or protected with tert-butoxycarbonyl group or benzyloxycarbonyl group.

Any of the above-mentioned condensation reactions can be promoted by the addition of preferably an organic base (e.g. triethylamine, N-methylpiperidine, 4-N,N-dimethylaminopyridine). The reaction temperature ranges usually from $-20°$ to $+50°$ C., preferably from $0°$ C. to about room temperatures. Examples of solvents to be usually employed include dioxane, tetrahydrofuran, acetonitrile, pyridine, N,N-dimethylformamide, dimethyl sulfoxide, N-methylpyrrolidone, chloroform and methylene chloride, and these can be used singly or as a mixture.

The conversion of cyano group into an amidino group in the method c) can be conducted by a per se known method, for example, allowing the nitrile to react with hydrogen sulfide and a base such as triethylamine to give thioamide, then methylating the thioamide with, for example, methyl iodide in acetone, followed by allowing the resultant methyl thioformimidolyl compound (i.e. the compound of formula (IV) in which the group $-C(=NH)SCH_3$) is present in place of cyano group) to react with ammonium acetate.

Also, the reduction of cyano group to an amino group in the method (C) can be conducted by a per se known method, preferably a catalytic reduction with use of a catalyst such as Pd.

The conversion of an amino group into a guanidino group in the method d) can be conducted by a per se known method, for example, allowing S-methyl isothiourea sulfate to react with the amino compound (VII) in the presence of a base such as sodium carbonate or sodium hydroxide. As the solvent, use is made of methanol, ethanol, dioxane or N, N-dimethylformamide singly or a mixture of them. The reaction temperature ranges usually from room temperatures to $+100°$ C., preferably form $+40°$ C. to $+70°$ C.

The protective group of the carboxyl group contained in the product of the final method (e.g. in the formula (I), $Z^1$ or $Z^2$ is an ester group such as benzyl ester group or tert-butyl ester) can be removed by a per se known method. For example, a compound having a benzyl ester group can e converted to a carboxylic acid derivative by subjecting the former to hydrogenation in the presence of a precious metal catalyst such as palladium or platinum, and a compound having tert-butyl ester group can be converted to a carboxylic acid derivative by treatment of the former with an acid such as trifluoroacetic acid or hydrogen chloride.

While salts of the compound (I) can be in some cases obtained by the reaction for producing the compound (I) itself, they can be produced by adding, upon necessity, an acid, alkali or base.

Thus-obtained compound (I) of this invention can be isolated from the reaction mixture by a conventional separation and purification means such as extraction, concentration, neutralization, recrystallization, column chromatography and thin-layer chromatography.

In the compound (I), at least two stereoisomers can be present. These individual isomers or a mixture thereof are of course included in the scope of the present invention, and, when desired, these isomers can be individually produced.

By conducting the following reaction using respectively a single isomer of the above-mentioned starting compounds (III), (IV), (V), (VI) or (VII) and a single isomer of the below-mentioned starting compounds (IX), (X), (XII), (XIV), (XV), (XVI), (XVIII), (XVIII), (XIX), (XXI), or (XXIII), a single optical isomer of the compound (I) can be obtained. And, when the product is a mixture of two or more isomers, it can be separated into respective isomers by a conventional separation method, for example, a method of causing formation of a salt with an optically active acid (e.g. camphor sulfonic acid, tartaric acid and dibenzoyl tartaric acid), an optically active base (e.g. cinchonine, cinchonidine, quinine, quinidine, α-methylbenzylamine and dehydroabiethylamine), or various chromatographic means or fractional crystallization.

The starting compound (II) of this invention is a per se known compound, and the starting compounds shown by the formulae (III), (IV), (V) and (VI) can be produced in a manner analogous to per se known methods, and, depending on cases, they can be produced by the methods shown by the following reaction formulae. In the following description, the compound of the formula (III) is, in some instances, simply referred to as (III), and as to other compounds, the same is applied to in some instances.

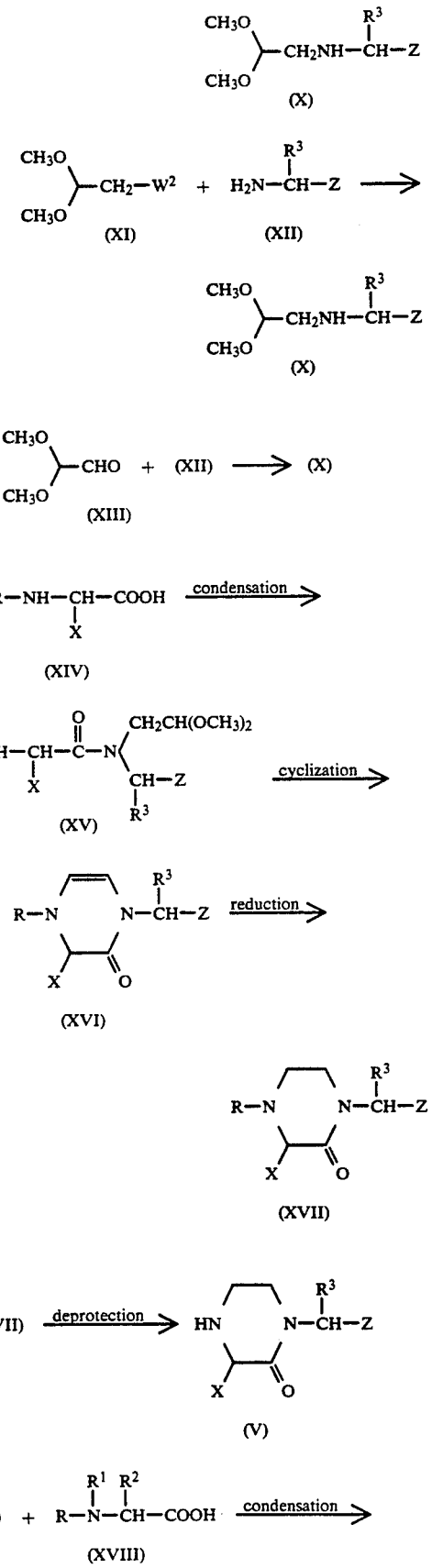

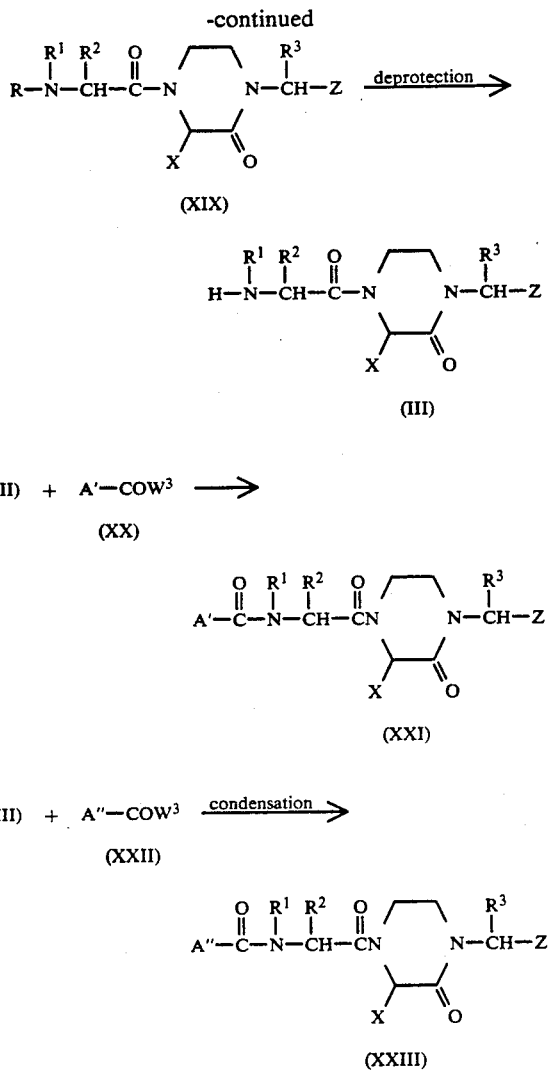

Further, the compound (X) is produced by subjecting the compound (XII) to condensation with the compound (XIII) under reductive conditions.

Examples of the reductive conditions include catalytic reduction using, as the catalyst, a metal such as platinum, palladium and rhodium or a mixture of the metal and an optional carrier, and reduction using a metallic hydride such as lithium aluminum hydride, lithium borohydride, lithium cyanoborohydride, sodium borohydride and sodium cyanoborohydride.

The reaction is conducted usually in the presence of an organic solvent (e.g. methanol, ethanol, ethyl ether, dioxane, methylene chloride, chloroform, benzene, toluene, dimethylformamide, dimethylacetamide). While the reaction temperature varies with the means of reduction, it is preferably within the range from $-20°$ C. to $+100°$ C. in general. This reaction proceeds satisfactorily under atmospheric pressure, and, depending on cases, the reaction can be conducted under elevated or reduced pressure.

The production of the compound (XV) by condensation of reaction of the compound (X) with the N-protected derivative of the amino acid (XIV) is a conventional peptide-forming reaction of amino acids, and the reaction can be conducted under substantially the same reaction conditions as in the condensation reaction of the compound (II) with the compound (III).

Cyclization of the thus-obtained compound (XV) into the cyclic compound (XVI) is the cyclization reaction with an acid catalyst. As the catalyst, use is made of, for example, an organic sulfonic acid such as p-toluenesulfonic acid, camphorsulfonic acid or methanesulfonic acid. The reaction is conducted by subjecting the compound (XV) to reaction usually in a solvent such as toluene, benzene, ethyl acetate or 1,2-dichloroethane at temperatures ranging from $0°$ to $100°$ C., preferably from $+30°$ C. to $+80°$ C. to give the compound (XVI).

The reduction of the compound (XVI) to the compound (XVII) is a reaction for reducing a double bond, and the compound (XVII) can be readily produced by, for example catalytic reduction using, as the catalyst, a metal such as platinum, palladium or Raney nickel, or a mixture of them with an optional carrier, or a reduction using a metalic hydride, for example, sodium borohydride or sodium cyano borohydride. The above reactions are conducted usually in the presence of an organic solvent (e.g. methanol, ethanol, dioxane, ethyl acetate). While the reaction temperature varies with the means of reduction, it is preferably in the range of from about $-20°$ C. to about $+100°$ C. While this reaction proceeds satisfactorily under normal pressure, it may be conducted, depending on cases, under elevated pressure. When R is a benzyloxycarbonyl group and the reduction is conducted catalytically, the reaction of removing the protective group of R proceeds simultaneously and the compound (V) can be obtained at one stroke.

Reactions for removing protective groups in (XVII) to (V) and (XIX) to (III) are conventional reactions for removing protective groups of amino groups in a peptide, and, in the case where R stands for a benzyloxycarbonyl group, the protective group can be removed by catalytic reduction using, as the catalyst, a metal such as platinum, palladium or rhodium. And, R stands for tert-butoxy carbonyl group, the protective group can be easily removed by the use of an acid such as trifluoroacetic acid or hydrogen chloride in an organic solvent such as methanol, ethanol, ethyl acetate or dioxane.

In the above reaction formulae, R is an amino protective group in amino acids, and stands for, for example, benzyloxycarbonyl group or tert-butoxycarbonyl group, $W^1$ stands for a halogen or a group represented by the formula $R^gSO_2$—O— (wherein $R^g$ stands for a lower ($C_{1-4}$) alkyl, trifluoromethyl, phenyl or p-tolyl), $W^2$ stands for halogen, and $W^3$ stands for a halogen or an active ester in the form of O=C—$W^3$, and other symbols are of the same meaning as defined above.

The method of producing the compound (II) shown by the above reaction formulae is explained as follows in further detail. The reaction for obtaining the compound (X) by allowing (VIII) to react with (IX) or allowing (XI) to react with (XII) is a conventional alkylation of an amino group. More specifically stating, the compound (VIII) and the compound (IX) or the compound (XI) and the compound (XII) are reacted usually at a temperature ranging from $0°$ C. to about $100°$ C. in the presence of a base (e.g. an inorganic base such as sodium carbonate, potassium carbonate, potassium hydrogencarbonate and cesium fluoride or an organic base such as triethylamine, pyridine and 4-N,N-dimethylaminopyridine) to give the compound (II). As the reaction solvent, use is made of an organic solvent such as acetonitrile, N,N-dimethylformamide, tetrahydrofuran, toluene or methylene chloride.

The condensation reaction of the compound (V) with an amino acid derivative (XVIII) and that of the compound (III) with the compound (XX) are reactions for forming amido-linkage. These reactions can be conducted in substantially the same manner as in the condensation of the compound (II) with the compound (III).

In the above-mentioned methods of producing the compound (I) and its intermediates, the compounds to be employed for the reactions may, unless undesirable effects are brought about, be in the forms of salts, for example, an inorganic acid salt such as hydrochloride, hydrobromide, sulfate, nitrate or phosphate, an organic acid salt such as acetate, tartrate, citrate, fumarate, maleate, toluenesulfonate or methanesulfonate, a metal salt such as sodium salt, potassium salt, calcium salt or aluminum salt, and a salt with a base such as triethylamine salt, guanidine salt, ammonium salt, hydrazine salt, quinine salt or cinchonine salt.

The compounds of the formula (I) (including their hydrates) and their salts inhibit both the binding of fibrinogen, fibronectin and von Willebrand factor to the fibrinogen receptor of blood platelets (glycoprotein IIb/IIIa) and the binding thereof and other adhesive aproteins, such as vitronectin, collagen and laminin, to the corresponding receptors on the surface of various types of cells. Hence the compounds of this invention influence cell-cell and cell-matrix interactions. They prevent, in particular, the development of blood platelet thrombosis and can be used in the therapy or prophylaxis of diseases such as peripheral arterial obstruction, acute myocardial infarction (AMI), deep vein thrombosis, pulmonary embolism, dissecting aneurysm, transient ischemic attack (TIA), stroke and other occlusive diseases, unstable angina, disseminated intravasular coagulation (DIC), sepsis, surgical or infective shock, postoperative and post-delivery trauma, angioplasty, cardiopulmonary bypass and coronary bypass, incompatible blood transfusion, amotio placentae, thrombotic thrombocytopenic purpura (TTP), asthma, chronic or acute renal diseases, diabetes, inflammations, arteriosclerosis, hemolytic uremic syndrome (HUS), symmetric peripheral necrosis, decubitus and allograft rejection in mammals including humans.

Further, the compound (I) of this invention can be used for enhancing the action of a thrombolytic agent and for preventing reobstruction after PTCR (percutaneous transluminal coronary recanalization), preventing reobstruction after PTCA (percutaneous transluminal coronary angioplasty), preventing thrombocytopenia due to dialysis, and the heparin induces thrombocytopenia, and prevention of thrombus caused by artificial blood vessel and organs. Besides, the compound (I) inhibits metastasis and can be used as an antitumor agent. Furthermore, the compound (I) inhibits invasion of bacteria to organs and thus can be used as an anti-infectious drug. The compound (I) can be used in combination with antithrombotic or anticoagulant agents such as heparin, aspirin and warfarin. Besides, the compound (I) inhibits bone resorption in osteoclast and thus can be used for the prophylaxis and the treatment of disorders of bone metabotism such as asteoporosis.

Pharmaceuticals containing the compound (I), a hydrate thereof or a salt thereof can be administered economically, for example, orally in the form of tablets, lacquered tablets, sugar-coated tablets, hard and soft gelatin capsules, solutions, emulsions or suspensions, or rectally, for example, in the form of suppositories, or as spray. However, administration can also take place parenterally, for example in the form of injectable solutions.

To prepare tablets, lacquered tablets, sugar-coated tablets and hard gelatin capsules, the active compound can be mixed with pharmaceutically inert, inorganic or organic excipients. Examples of such excipients which can be used for tablets, sugar-coated tablets and hard gelatin capsules are lactose, corn starch or derivatives thereof, talc, stearic acid or salts thereof. Examples of suitable excipients for soft gelatin capsules are vegetable oils, waxes, fats, semisolid and liquid polyols; however, no excipients whatever are necessary with soft gelatin capsules if the characteristic features of the active compound are appropriate.

Examples of suitable excipients for the preparation of solutions and syrups are water, polyols, sucrose, invert sugar and glucose, suitable examples for injectable solutions are water, alcohols, polyols, glycerol and vegetable oils, and suitable examples for suppositories are natural or hardened oils, waxes, fats and semiliquid or liquid polyols. The pharmaceutical products can additionally contain preservatives, solubilizers, stabilizers, wetting agents, emulsifiers, sweeteners, colorants, flavorings, salts to alter the osmotic pressure, buffers, coating agents or antioxidants.

The dosage of the active compound for controlling or preventing the diseases which are mentioned hereinbefore can vary within a wide range and should, of course, be adjusted to suit the individual circumstances in each particular case. In general a dose of about 0.1 to 20 mg/kg, preferably of about 0.5 to 4 mg/kg, per day ought to be appropriate on oral administration for adults. When the compound of the present invention is administered parenterally, typically intravenously, the preferable daily dosage per adult is about 0.01–2.0 mg/kg, preferably about 0.05–0.4 mg.

The following test examples and working examples will describe the present invention in further detail, but they are not intended to limit the present invention in any way.

TEST EXAMPLE 1 [I] Inhibitory action on guinea pig platelet aggregation

Blood was collected in 3.15% sodium citrate (1 ml for 9 ml of blood) by cardiac puncture from male guinea pig. The blood was centrifuged at 1000 g for 3 to 5 seconds at room temperature to obtain platelet rich plasma (PRP). The PRP was further centrifuged at 1000 g for 10 minutes to obtain platelet poor plasma (PPP). The number of platelets was measured using an automatic blood cell counter (Sysmex E2500, Toaiyoudensi). The platelet density of PRP was adjusted to $400,000/\mu l$ with PPP. Platelet aggregation was measured using an 8-channel aggregometer (NBS HEMA TRACER VI Niko Bioscience Inc.). The PRP (250 $\mu l$) was preincubated at 37° C. for 2 minutes. and then incubated for 2 minutes. with 25 $\mu l$ of physiological saline or various concentrations of test drugs followed by stimulation with ADP (final concentration: 1 $\mu M$). By comparing the maximum aggregation rates of the control and those of test drugs, the inhibitory rates were determined. The results are shown in [Table 1]–[Table 3].

[II] Inhibitory action on human platelet aggregation

Human blood was collected in 3.8% sodium citrate (1 ml for 9 ml of blood) by venipuncture from healthy male volunteers. The blood was centrifuged at 1000 g for 3 to 5 seconds at room temperature to obtain platelet rich plasma (PRP). The PRP was further centrifuged at 1000 g for 10 minutes to obtain platelet poor plasma (PPP). The number of platelets was measured using an automatic blood cell counter (Sysmex E2500, Toaiyoudensi). The platelet density of PRP was adjusted to 300,000/µl with PPP. Platelet aggregation was measured using an 8-channel aggregometer (NBS HEMA TRACER VI Niko Bioscience Inc.). The PRP (250 µl) was preincubated at 37° C. for 2 minutes. and then incubated for 2 minutes. with 25 µl of physiological saline or various concentrations of test drugs followed by stimulation with ADP (final concentration: 3 µM). By comparing the maximum aggregation rates of the control and those of test drugs, the inhibitory rates were determined. The results are shown in [Table 1]–[Table 3].

TABLE 1

$$HN\diagdown_{H_2N}\!\!\!\!\!\!\!\!\!\!\!\!\!\!\!\!\!\!\!\!\!\!/\!\!-D-CON-\underset{R^1}{\overset{}{C}}H-CON\diagup\diagdown N-\underset{}{\overset{R^3}{C}}H-Z$$

| W. E. No. | D | $R^1$ $R^2$<br>$-N-CH-CO-$ | X | $R^3$ | Z | Inhibitory effect on platelet aggregation in vitro (IC$_{50}$: µM) | |
|---|---|---|---|---|---|---|---|
| | | | | | | guinea pig | man |
| 5 | —NH—CH$_2$—⟨cyclohexyl⟩— | Gly | CH$_2$COOH | H | COOH | 3.8 | 1.1 |
| 4 | —NH—(CH$_2$)$_4$— | Gly | CH$_2$COOH | H | COOH | 5.0 | 3.5 |
| 35 | —NH—CH$_2$—⟨cyclohexyl⟩— | Gly | H | H | COOH | 5.2 | 1.1 |
| 32 | —NH—CH$_2$—⟨cyclohexyl⟩— | Gly | CH$_2$CH$_2$COOH | H | COOH | 3.1 | 0.96 |
| 22 | —NH—CH$_2$—⟨cyclohexyl⟩— | Gly | CH$_2$CONH$_2$ | H | COOH | 4.4 | 0.72 |
| 37 | —NH—CH$_2$—⟨cyclohexyl⟩— | Phe | H | H | COOH | 7.0 | 0.52 |
| 12 | —NH—CH$_2$—⟨cyclohexyl⟩— | Sar | CH$_2$COOH | H | COOH | 1.1 | 0.70 |

TABLE 2

$$HN\diagdown_{H_2N}\!\!\!\!\!\!\!\!\!\!\!\!\!\!\!\!\!\!\!\!\!\!/\!\!-D-CON-\underset{R^1}{\overset{}{C}}H-CON\diagup\diagdown N-\underset{}{\overset{R^3}{C}}H-Z$$

| W. E. No. | D | $R^1$ $R^2$<br>$-N-CH-CO-$ | X | $R^3$ | Z | Inhibitory effect on platelet aggregation in vitro (IC$_{50}$: µM) | |
|---|---|---|---|---|---|---|---|
| | | | | | | guinea pig | man |
| 38 | —N⟨piperidinyl⟩— | Gly | CH$_2$COOH | H | COOH | 9.6 | 1.6 |

TABLE 2-continued $$\text{HN} \diagdown \text{C-D-CON-CH-CON} \diagup \diagdown \text{N-CH-Z}$$
with $R^1, R^2$ on the CH-CO middle, $R^3$ on N-CH, and a ring containing X (S) and =O, with $H_2N$ on the amidine.

| W. E. No. | D | $R^1 R^2$ −N−CH−CO− | X | $R^3$ | Z | Inhibitory effect on platelet aggregation in vitro (IC$_{50}$: μM) guinea pig | man |
|---|---|---|---|---|---|---|---|
| 8 | −NH−CH$_2$−(phenyl)− | Gly | CH$_2$COOH | H | COOH | 1.3 | 0.66 |
| 10 | −NH−(phenyl)− | Gly | CH$_2$COOH | H | COOH | 0.34 | 0.26 |
| 16 | −NH−CH$_2$−(cyclohexyl) | Gly | CH$_2$Ph | H | COOH | 4.6 | 0.99 |

TABLE 3

| W. E. No. | Inhibitory effect on platelet aggregation in vitro (IC$_{50}$:μM) | |
|---|---|---|
| | guinea pig | man |
| 39 | 0.165 | 0.11 |
| 45 | 1.6 | 1.5 |
| 46 | 0.13 | 0.23 |
| 47 | 2.8 | 4.2 |
| 50 | 0.345 | |
| 51 | 0.37 | 0.46 |
| 54 | 4.1 | 0.66 |
| 55 | 0.21 | 0.094 |
| 57 | 1.75 | 2.6 |
| 59 | 0.056 | 0.048 |
| 60 | 0.078 | 0.093 |
| 61 | 0.16 | 0.13 |
| 63 | 0.46 | 0.72 |
| 65 | 4.6 | |
| 66 | 0.066 | 0.052 |
| 69 | 1.5 | 1.6 |
| 71 | 0.11 | 0.074 |
| 76 | 0.11 | 0.15 |
| 77 | 2.5 | 4.7 |
| 80 | 0.12 | 0.11 |
| 81 | 2.3 | |
| 84 | 0.11 | 0.12 |
| 85 | 4.1 | 5.6 |
| 87 | 0.15 | 0.18 |
| 88 | 0.084 | 0.14 |
| 89 | 0.20 | 0.38 |

TEST EXAMPLE 2 Inhibition of fibrinogen binding to GPIIb/IIIa (1) Cultibation of Cells Derived from Human Erythroleukemia (Hereinafter Referred to as HEL Cells)

HEL cells (HEL 92. 1. 7; ATCC No. TIB180) were purchased from ATCC (Rockville, Md., U.S.A.). The cells were grown in RPMI medium containing 40 mM N-2-hydroxyethylpiperazin-N'-2-ethanesulfonic acid (hereinafter referred to as HEPES) (pH 7.0), 100 μg/ml of Kanamycin and 10% FCS (GIBCO Laboratories, Grand Island, N.Y., U.S.A.). Cultivation was conducted at 37° C in the presence of 5% CO$_2$. The culture was subcultured successively at intervals of 3 to 4 days so as to give 4 to 5 times dilution each.

(2) Purification of GPIIb/IIIa from HEL Cells

Purification of GPIIb/IIIa was performed using the following modification of the method of L. A. Fitzgerald et al. [*J. Biol. Chem.*, 262, 3936 (1987)]. The purification was conducted at room temperature unless specifically mentioned. From 7 L of the culture broth on 7th day of the cultibation (floating cells), the cells were collected by centrifugation (1,000×g, 10 minutes, 4° C.), which were washed with 20 mM Tris-HCl(pH 7.5) containing 1 mM EDTA and 150 mM NaCl. The cells were suspended in 80 ml of a solubilized buffer [20 mM Tris-HCl, 150 mM NaCl, 1% Triton X-100, 1 mM MgCl$_2$, 1 mM CaCl$_2$, 0.1 mM (p-amidinophenyl)methanesulfonyl fluoride (hereinafter referred to as APMSF), 10 nM leupeptin, 0.02% NaN$_3$, pH 7.4)].

The cell suspension was gently mixed for 30 minutes at 4° C. to solubilize GPIIb/IIIa. The suspension was subjected to centrigugation (100,000×g, one hour) at 4° C. to remove cell debris to obtain a cell-extraction solution (60 ml). The cell-extraction solution was allowed to pass through Heparin-Sepharose CL-6B column (Pharmacia LKB Biotechnology AB, Uppsala, Sweden, φ 1.6× 10.5 cm, 20 ml/hr) equilibrated with a column buffer (20 mM Tris-HCl, 150 mM NaCl, 0.1% Triton X-100, 1 mM MgCl$_2$, 1 mM CaCl$_2$, 0.1 mM APMSF, 1 nM leupeptin, 0.05% NaN$_3$, pH 7.4) to remove thrombospondin. The fraction which passed through the column was charged on the ConA-Sepharose column (Pharmacia LKB, φ 1.0×15 cm, 20 ml/hr) to allow GPIIb/IIIa to be adsorbed thereon, then GPIIb/IIIa was eluted with column buffer solution containing 0.5 M methyl α-D-mannopyranoside. The eluate thus obtained was allowed to pass through the DEAE-Toyopearl 650 M column (Tosoh, φ 1.6×10.5 cm, 20 ml/hr) equilibrated with the same column buffer to remove contaminating proteins. The resulting fraction was concentrated by using Amicon YM10 membrane at 4° C., and the concentrate was subjected to gel-filtration by means of the Sephacryl S-300 column (Pharmacia LKB, φ 1.6×95 cm, 30 ml/hr) to afford 2.3 mg of the purified GPIIb/IIIa.

(3) Biotinylation of Human Fibrinogen

Biotinylation of human fibrinogen was performed by the following procedure [I. F. Charo et al., *J. Biol. Chem.*, 266, 1415 (1991)]. Human fibrinogen (Kabi Vitrum AB, Stockholm, Sweden) was dissolved in PBS so as to make its concentration 5 mg/ml. The solution was dialyzed overnight at 4° C. against 1 L of 0.1 M NaHCO$_3$-0.1 M NaCl (pH 8.2). Insolubles were then removed by centrifugation (100,000×g, 30 minutes), and the solution was diluted with the same buffer to the protein concentration of 1 mg/ml. To thus-diluted solution was added powdery sulfo-N-hydroxysuccinimidobiotin (Pierce Chemical Co., Rockford, Ill., U.S.A.) so as to make its final concentration 0.2 mg/ml and gently mixed to perform biotinylate fibrinogen. The resultant was subjected to dialysis against 50 mM Tris-HCl (pH 7.4) - 100 mM NaCl-0.05% NaN$_3$. The dialysate was distributed and stored at 4° C.

(4) Inhibition Assay for Fibrinogen Binding to GPIIb/IIIa

This experiment was performed using a modification of the method described in the above-mentioned I. F. Charo et al. report. The purified GPIIb/IIIa was diluted with the buffer A (20 mM Tris-HCl, 150 mM NaCl, 1 mM CaCl$_2$, 0.02% NaN$_3$, pH 7.4) to a concentration of 1 μg/ml. The diluted solution was added to 96-well microtiter plates (MaxiSorp; Nunc, Denmark) at 100 μl per well, which were left standing at 4° C. overnight to allow GPIIb/IIIa to be adsorbed on the microplates. The plate was aspirated, and then 150 μl of the buffer B (35 mg/ml BSA, 50 mM Tris-HCl, 100 mM NaCl, 2 mM CaCl$_2$, 0.02%, NaN$_3$, pH 7.4) was added to the plate, and blocking was performed at 30° C. for 2 hours. The plate was washed twice with 250 μl each of the buffer C (1 mg/ml BSA, 50mM Tris-HCl, 100 mM NaCl, 2 mM CaCl$_2$, pH 7.4). To the plate was added the buffer C (100 μl) containing biotinylated fibrinogen (1 nM=330 ng/ml) and an antagonist, and the plate was kept at 30° C. for 3 hours or at room temperatures overnight. The plate was washed twice with 250 μl each of the buffer C, to which was added 100 μl of an anti-biotin alkaline phosphatase conjugate (Sigma Chemical Co., St. Louis, Mo., U.S.A.; 200 times dilution with buffer solution C), and the reaction was allowed to proceed for one hour at 30° C. The plate was washed twice with 250 μl each of the buffer C, to which was added 100 μl of p-nitrophenyl phosphate solution (alkaline phosphatase color-development kit; Bio-Rad Laboratories, Richmond, Calif., U.S.A.). The reaction was allowed to proceed at room temperature until the absorbance at 405 nm reached 1.0 to 1.2 (1 to 3 hours). Then, 4N NaOH was added to stop the reaction. The absorbance at 405 nm was determined by using Titerteck Multiscan MC (Flow Laboratories, Finland). Incidentally, DMSO showed inhibitory action on this assay, and it was found that DMSO was to be diluted to a concentration of 0.1% or below.

IC$_{50}$ was defined as the concentration of an inhibitor showing 50% absorbance, when the absorbance shown in the case of non-addition of biotinylated fibrinogen was assumed 0%, and when the absorbance shown in the case of adding biotinylated fibrinogen and non-addition of an inhibitor was assumed 100%. Practically, a preliminary study was conducted by using 10-times dilution series, then experiments were performed by using 3-times dilution series around IC$_{50}$ while 10-times dilution series for others. From the mean of duplicate determinations for one dilution solution, IC$_{50}$ was determined. The results are shown in [Table 4].

TABLE 4

| W.E. No. of Compounds | Inhibition of fibrinogen binding to GPIIb/IIIa (IC$_{50}$;nM) |
| --- | --- |
| 5 | 20 |
| 6 | 46 |
| 8 | 18 |
| 9 | 73 |
| 10 | 4.8 |
| 12 | 10 |
| 16 | 32 |
| 22 | 23 |
| 32 | 15 |
| 37 | 7.9 |
| 38 | 21 |
| 39 | 1.0 |
| 45 | 8.1 |
| 46 | 2.5 |
| 47 | 18 |
| 48 | 15 |
| 50 | 21 |
| 54 | 6.1 |
| 55 | 0.42 |
| 57 | 20 |
| 59 | 0.49 |
| 60 | 0.91 |
| 63 | 8.9 |
| 65 | 98 |
| 66 | 0.20 |
| 69 | 19 |
| 71 | 0.92 |
| 76 | 1.0 |
| 77 | 45.0 |
| 80 | 0.89 |
| 81 | 37.0 |
| 84 | 1.0 |
| 85 | 32.0 |
| 87 | 1.6 |
| 88 | 2.3 |
| 89 | 3.6 |

From the above results, it was found that the compounds of this invention inhibit the binding of GPIIb/IIIa to fibrinogen at a remarkably low concentration as GPIIb/IIIa antagonist.

WORKING EXAMPLE 1

N-(2,2-Diethoxyethyl)glycine t-butyl ester

To a mixture of 20 g of aminoacetaldehyde diethyl acetal, 28 g of potassium carbonate and 100 ml of dimethylformamide was added dropwise 15 g of t-butyl ester of chloroacetic acid while stirring at room temperature in the course of 30 minutes. The mixture was stirred for 12 hours at the same temperature, then the reaction mixture was diluted with ether, followed by washing with water. The ether layer was dried over anhydrous magnesium sulfate, then concentrated under reduced pressure to give a crude product. The crude product was purified by means of a silica gel chromatography using an eluent (n-hexane:ethyl acetate=1:1) to afford 16.8 g of the title compound as a colorless oily product.

Elemental Analysis for C$_{12}$H$_{25}$NO$_4$(247.33):
Calcd.: C, 58.27; H, 10.19; N, 5.66.
Found: C, 58.01; H, 10.33; N, 5.46.

WORKING EXAMPLE 2

N-(N-Benzyloxycarbonyl-O⁴-t-butyl-L-aspartyl)-N-(2,2-diethoxyethyl)glycine t-butyl ester To a mixture of 6.8 g of N-(2,2-diethoxyethyl)glycine t-butyl ester, 8.1 g of N-benzyloxycarbonyl-L-aspartic acid-$\beta$-t-butyl ester and 50 ml of dimethylformamide were added 5.5 g of diethyl cyanophosphonate, then 2.8 g of triethylamine at 0° C. in the course of 5 minutes. The mixture was stirred for 30 minutes at the same temperature, then for 12 hours at room temperatures. The reaction mixture was diluted with ethyl acetate, then washed with water. The ethyl acetate layer was dried over anhydrous magnesium sulfate and concentrated under reduced pressure to give a crude product. The crude product was purified by means of chromatography on silica gel using an eluent (n-hexane:ethyl acetate=4:1) to afford 6.9 g of the title compound as a colorless oily product.

Specific optical rotation: $[\alpha]_D^{23}$ −20.9° (C=0.89, MeOH)

Elemental Analysis for $C_{28}H_{44}N_2O_9$(552.66):
Calcd.: C, 60.85; H, 8.02; N, 5.07.
Found: C, 60.59; H, 8.25; N, 4.88.

WORKING EXAMPLE 3

(S)-2-Oxopiperazine-1,3-diacetic acid di-t-butyl ester hydrochloride

In 500 ml of toluene were dissolved 11 g of N-(N-benzyloxycarbonyl-O⁴-t-butyl-L-aspartvl-)-N-2,2-diethoxy-ethyl)glycine t-butyl ester and 380 mg of p-toluenesulfonic acid. The solution was stirred for one hour on a water bath of 50° C. under nitrogen streams. The reaction mixture was left standing for cooling, then washed with a saturated aqueous solution of sodium hydrogencarbonate and concentrated under reduced pressure. The concentrate was dissolved in 300 ml of methanol, to which were added 1.0 g of 10% palladium-carbon and 3.5 ml of 4N hydrochloric acid - dioxane solution. The mixture was stirred vigorously for 7 hours under hydrogen streams. The catalyst was removed, and the solution was concentrated under reduced pressure to give 4.8 g of the title compound as a colorless oily product. This product was process with ether to give amorphous powder.

Specific optical rotation : $[\alpha]_D^{23}$ −11.9° (C=1.0, MeOH)

Elemental Analysis for $C_{16}H_{28}N_2O_5 \cdot HCl$(364.87):
Calcd.: C, 52.67; H, 8.01; N, 7.68.
Found: C, 52.51; H, 8.19; N, 7.81.

WORKING EXAMPLE 4

(S)-4-Glycyl-2-oxopiperazine-1,3-diacetic acid di t-butyl ester hydrochloride

To a mixture of 3.7 g of (S)-2-oxopiperazine-1,3-diacetic acid di-t-butyl ester hydrochloride, 3.3 g of N-benzyloxycarbonyl glycine and 10 ml of dimethylformamide were added dropwise, while stirring at 0° C., 3.1 g of diethyl cyanophosphonate then 3.2 g of triethylamine in the course of 10 minutes. The mixture was stirred for one hour at the same temperature then for 3 hours at room temperature. The reaction mixture was poured into ice-water, which was subjected to extraction with ethyl acetate. The extract solution was dried over anhydrous magnesium sulfate and concentrated to give a crude product. The crude product was dissolved in 30 ml of methanol, to which were added 1 g of 10% palladium-carbon and 1.8 ml of 4N HCl-dioxane solution. The mixture was stirred for one hour at room temperature under hydrogen. The catalyst was removed, and the reaction mixture was concentrated under reduced pressure to afford 2.6 g of the title compound as a colorless oily product. This product was processed with ether to give colorless powder.

Specific optical rotation: $[\alpha]_D^{23}$ +79.7° (C=1.1, MeOH)

Elemental Analysis for $C_{18}H_{31}N_3O_6 \cdot HCl$(421.92):
Calcd.: C, 51.21; H, 7.64; N, 9.96.
Found: C, 50.99, H, 7.64; N, 9.88.

WORKING EXAMPLE 5

(S)-4-(trans-4-Guanidinomethylcyclohexylcarbonyl-glycyl)-2-oxopiperazine-1,3-diacetic acid hydrochloride To a mixture of 285 mg of trans-4-guanidinomethyl-cyclo hexane carboxylic acid hydrochloride, 215 mg of N-hydroxy-5-norbornene-2,3-dicarboxyimide and 2 ml of dimethylformamide was added 310 mg of dicyclohexylcarbodiimide. The mixture was stirred for one hour at 0° C. then for two hours at room temperature. Insolubles were filtered off, then the filtrate was cooled with ice and there were added 500 mg of (S)-4-glycyl-2-oxopiperazine-1,3-diacetic acid di-t-butyl ester hydrochloride, then 120 mg of triethylamine. The mixture was stirred for one hour at the same temperature. The reaction mixture was concentrated under reduced pressure to give a crude product, which was dissolved in 3 ml of methylene chloride. To the solution was added 3 ml of trifluoroacetic acid at 0° C. The mixture was stirred for one hour at the same temperature, then for one hour at room temperature, followed by concentration under reduced pressure. The concentrate was dissolved in 10 ml of 1N HCl-dioxane. The solution was left standing for one hour at room temperature, then concentrated under reduced pressure. This procedure was repeated to give a crude product, which was subjected to a $C_{18}$-ODS column chromatography using a mixture of water and acetonitrile (97:3) as the eluent. The relevant fraction was freeze-dried to afford 200 mg of the title compound as amorphous powder.

Specific optical rotation: $[\alpha]_D^{23}$+65.8° (C=0.25, MeOH)

Elemental Analysis for $C_{19}H_{30}N_6O_7 \cdot HCl$(490.94):
Calcd.: C, 46.48; H, 6.36; N, 17.12.
Found: C, 46.19; H, 6.60; N, 17.02.

By substantially the same procedure as in Working Example 5, the following compounds can be synthesized.

| | X | Rational Formula | Calcd. (Found) | $[\alpha]_D^{23}$ (C, MeOH) |
|---|---|---|---|---|
| Working Example 6 | $-(CH_2)_4-$ | $C_{16}H_{26}N_6O_2 \cdot HCl \cdot H_2O$ | C, 40.79; H, 6.39; N, 17.81 (C, 40.98; H, 6.23; N, 17.92) | +83.0° (0.28) |
| Working Example 7 | $-(CH_2)_3-$ | $C_{15}H_{24}N_6O_2 \cdot HCl$ | C, 40.98; H, 5.87; N, 19.16 (C, 41.24; H, 5.77; N, 19.24) | +75.3° (0.32) |
| Working Example 8 | 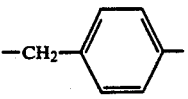 | $C_{19}H_{24}N_6O_7 \cdot HCl$ | C, 46.86; H, 5.48; N, 17.18 (C, 47.06; H, 5.20; N, 17.33) | +58.5° (0.18) |
| Working Example 9 | 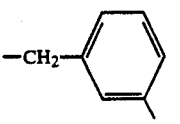 | $C_{19}H_{24}N_6O_2 \cdot HCl$ | C, 47.01; H, 5.48; N, 17.21 (C, 47.06; H, 5.20; N, 17.33) | +78.5° (0.25) |
| Working Example 10 | 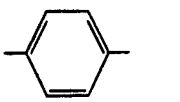 | $C_{18}H_{22}N_6O_2 \cdot HCl$ | C, 45.72; H, 5.17; N, 17.81 (C, 45.91; H, 4.92; N, 17.85) | +78.6° (0.30) |

WORKING EXAMPLE 11

(S)-4-(N-Methylglycyl)-2-oxopiperazine-1,3-diacetic acid di-t-butyl ester hydrochloride A mixture of 1.3 g of (S)-2-oxopiperazaine-1,3-diacetic acid di-t-butyl ester hydrochloride and 1.1 g of N-benzyloxycarbonyl sarcocine was subjected to substantially the same procedure as in Working Example 4 to afford 700 mg of the title compound as amorphous powder.

Elemental Analysis for $C_{19}H_{33}N_3O_6 \cdot HCl(435.95)$:
Calcd.: C, 52.35; H, 7.86; N, 9.64.
Found: C, 52.29; H, 7.93; N, 9.35.

WORKING EXAMPLE 12

(S)-4-[[N-(trans-4-Guanidinomethylcyclohexylcarbonyl)]-N-methyl glycyl]-2-oxopiperazine-1,3-diacetic acid hydrochloride (S) -4-(N-Methylglycyl)-2-oxopiperazine-1,3-diacetic acid di-t-butyl ester hydrochloride (500 mg) was subjected to substantially the same procedure as in Working Example 5 to obtain 220 mg of the title compound as amorphous powder.

Specific optical rotation: $[\alpha]_D^{23} +51.2°$ (C=0.25, MeOH)

Elemental Analysis for $C_{20}H_{32}N_6O_7 \cdot HCl(504.97)$:
Calcd.: C, 47.57, H, 6.59; N, 16.64.
Found: C, 47.50; H, 6.88; N, 16.48.

WORKING EXAMPLE 13

N-(N-Benzyloxycarbonyl-L-phenylalanyl)-N-(2,2-diethoxy ethyl)glycine t-butyl ester A mixture of 11.0 g of N-(2,2-diethoxyethyl)glycine t-butyl ester, 13.3 g of N-benzyloxycarbonyl-L-phenylalanine and 50 ml of dimethylformamide was cooled to 0° C., and there were added dropwise 9.4 g of diethyl cyanophosphonate, then 5.9 g of triethylamine. The mixture was stirred for one hour at the same temperature, then for 5 hours at room temperature. The reaction mixture was diluted with ethyl acetate, which was poured into ice-water. The ethyl acetate layer was dried over anhydrous magnesium sulfate, then concentrated under reduced pressure to give a crude product. The crude product was purified by means of chromatography on silica gel using an eluent (n-hexane:ethyl acetate=9:1) to afford 20.0 g of the title compound as a colorless oily product.

Specific optical rotation: $[\alpha]_D^{23} -11.1°$ (C=1.1, MeOH)

Elemental Analysis for $C_{29}H_{40}N_2O_7(528.64)$:
Calcd.: C, 65.89; H, 7.63; N, 5.30.
Found: C, 65.79; H, 7.61; N, 5.30.

WORKING EXAMPLE 14

(S)-3-Benzyl-2-oxopiperazine-1-acetic acid t-butyl ester hydrochloride

N-(N-Benzyloxycarbonyl-L-phenylalanyl)-N-(2,2-diethoxy ethyl)glycine t-butyl ester (9.0 g) was subjected to substantially the same procedure as in Working Example 3 to obtain 4.3 g of the title compound as colorless prisms, m.p. 206-208° C. (recrystallized from ethanol).

Specific optical rotation: $[\alpha]_D^{23} -93.2°$ (C=0.95, MeOH)

Elemental Analysis for $C_{17}H_{24}N_2O_3 \cdot (340.85)$:
Calcd.: C, 59.91; H, 7.39; N, 8.22.
Found: C, 59.89; H, 7.44; N, 8.23.

WORKING EXAMPLE 15

(S)-3-Benzyl-4-glycyl-2-oxopiperazine-1-acetic acid t-butyl ester hydrochloride

In 20 ml of acetonitrile was dissolved 2.45 g of N-benzyloxycarbonyl glycine. To the solution was added, at 0° C., 1.3 g of dicyclohexylcarbodiimide. The mixture was stirred for one hour at the same temperature, then for two hours at room temperature. Insolubles were filtered off. To the filtrate were added 1.0 g of (S)-3-benzyl-2-oxopiperazine-1-acetic acid t-butyl ester hydrochloride, 35 mg of 4-dimethylaminopyridine and 1.1 g of triethylamine. The mixture was stirred for 48 hours. The reaction mixture was concentrated under reduced pressure. The concentrate was dissolved in methylene chloride, which was washed with a 5% aqueous solution of potassium hydrogensulfate then with a 10% aqueous solution of sodium hydrogencarbonate. The methylene chloride layer was dried over magnesium sulfate, followed by concentration under reduced pressure to give a crude product. The crude product was dissolved in 30 ml of methanol, to which were added 100 mg of 10% palladium-carbon and 4N HCl-dioxane solution. The mixture was stirred for one hour at room temperature in hydrogen streams. The catalysts were filtered off, and the filtrate was concentrated under reduced pressure to afford 400 mg of the title compound as a colorless oily product. This product was processed with ether to give amorphous powder.

Elemental Analysis for $C_{19}H_{27}N_3O_4 \cdot HCl(397.90)$:
Calcd.: C, 57.35; H, 7.09; N, 10.56.
Found: C, 57.17; H, 7.13; N, 10.45.

WORKING EXAMPLE 16
(S)-3-Benzyl-4-(trans-4-guanidinomethylcyclohexylcarbonyl glycyl)-2-oxopiperazine-1-acetic acid hydrochloride (S)-3-Benzyl-4-glycyl-2-oxopiperazine-1-acetic acid t-butyl ester (500 mg) was subjected to substantially the same procedure as in Working Example 5 to give 235 mg of the title compound as amorphous powder.

Specific optical rotation: $[\alpha]_D^{23} + 68.7°$ (C=0.35, MeOH)

Elemental Analysis for $C_{24}H_{34}N_6O_5 \cdot HCl(523.03)$:
Calcd.: C, 55.11; H, 6.74; N, 16.07.
Found: C, 55.01; H, 6.98; N, 15.79.

WORKING EXAMPLE 17
N-(N-t-Butoxycarbonyl-$O^4$-benzyl-L-aspartyl)-N-(2,2-diethoxyethyl)glycine t-butyl ester N-Diethoxyethylglycine t-butyl ester (16.6 g) and N-t-butoxycarbonyl-L-aspartic acid-$\beta$-benzyl ester (21.7 g) were subjected to substantially the same procedure as in Working Example 2 to give 22 g of the title compound as a colorless oily product.

Specific optical rotation: $[\alpha]_D^{23} - 18.9°$ (C=0.30, MeOH)

Elemental Analysis for $C_{23}H_{44}N_2O_9(552.66)$:
Calcd.: C, 60.85; H, 8.02; N, 5.07.
Found: C, 60.81; H, 8.19; N, 4.95.

WORKING EXAMPLE 18
(S)-4-t-Butoxycarbonyl-1-t-butoxycarbonylmethyl-2-oxopiperazine-3-acetic acid N-(N-t-Butoxycarbonyl-$O^4$-benzyl-L-aspartyl)-N-(2,3-diethoxyethyl)glycine t-butyl ester (15 g) was subjected to substantially the same procedure as in Working Example 3 to give 7.4 g of the title compound as a colorless oily product.

Elemental Analysis for $C_{17}H_{28}N_2O_7(372.42)$:
Calcd.: C, 54.83; H, 7.58; N, 7.52.
Found: C, 54.69; H, 7.87; N, 7.41.

WORKING EXAMPLE 19
(S)-3-Carbamoylmethyl-2-oxopiperazine-1-acetic acid hydrochloride A mixture of 3.0 g of (S)-4-t-butoxycarbonyl-1-t-butoxycarbonylmethyl-2-oxopiperazine-3-acetic acid, 1.2 g of N-hydroxysuccinimide and 50 ml of dioxane was cooled to 0° C., to which was added 2.5 g of dicyclohexylcarbodiimide. The mixture was stirred for one hour at the same temperature, then for one hour at room temperature, followed by removing insolubles by filtration. To a mixture of 10 ml of 25% aqueous ammonia and 50 ml of dioxane was added dropwise, while stirring vigorously, the active ester solution prepared as above in the course of 5 minutes. The reaction mixture was concentrated under reduced pressure. The concentrate was dissolved in methylene chloride, which was washed with water. The methylene chloride layer was dried over anhydrous magnesium sulfate then concentrated under reduced pressure to give an oily product. The oily product was dissolved in 30 ml of trifluoroacetic acid. The solution was left standing for one hour at room temperature and then subjected to evaporation to dryness. The residue was dissolved in 4N HCl-dioxane and then left standing for one hour, followed by concentration under reduced pressure. This procedure was repeated to give 1.1 g of the title compound as a colorless oily product. This product was processed with ether to give amorphous powder.

Elemental Analysis for $C_8H_{13}N_3O_4 \cdot HCl(251.67)$:
Calcd.: C, 38.18; H, 5.61; N, 16.70.
Found: C, 38.01; H, 5.78; N, 16.40.

WORKING EXAMPLE 20
(S)-3-Carbamoylmethyl-2-oxopiperazine-1-acetic acid benzyl ester hydrochloride To a mixture of 1.8 g of (S)-3-carbamoylmethyl-2-oxopiperazine-1-acetic acid hydrochloride, 3.0 g of sodium carbonate, 20 ml of dioxane and 20 ml of water was added, while stirring vigorously, 2.0 g of di-t-butyl bicarbonate. The mixture was stirred vigorously for 2 hours at 0° C. The reaction mixture was concentrated to half of its original volume. The concentrate was washed with ether and there was added 20 ml of a 10% aqueous solution of potassium hydrogensulfate, followed by extraction with methylene chloride. The extract solution was dried over anhydrous magnesium sulfate and then concentrated under reduced pressure to give an oily product. The oily product was dissolved in 10 ml of dimethylformamide, to which were added 720 mg of potassium hydrogencarbonate and 1.0 g of benzyl bromide. The mixture was stirred for 12 hours at room temperature. The reaction mixture was diluted with ethyl acetate, washed with water and dried over anhydrous magnesium sulfate, followed by concentration under reduced pressure to give a crude product. The crude product was dissolved in 30 ml of 2N HCl-ethyl acetate, and the solution was stirred for one hour at room temperature. The reaction mixture was concentrated under reduced pressure to give an oily product, which was processed with ether to afford 1.0 g of the title compound as amorphous powder.

Specific optical rotation : $[\alpha]_D^{23} - 8.4°$ (C=0.94, MeOH)

Elemental Analysis for $C_{15}H_{19}N_3O_4 \cdot HCl(341.79)$:
Calcd.: C, 52.71; H, 5.90; N, 12.29.
Found: C, 52.55; H, 6.02; N, 12.06.

WORKING EXAMPLE 21
(S)-3-Carbamoylmethyl-4-glycyl-2-oxopiperazine-1-acetic acid benzyl ester hydrochloride In 10 ml of acetonitrile was dissolved 1.4 g of N-t-butoxycarbonyl glycine. To the solution was added at 0° C. 890 mg of dicyclohexyl carbodiimide. The mixture was stirred for one hour at the same temperature, then for 3 hours at room temperature. Insolubles were filtered off. To the filtrate were added 900 mg of (S)-3-carbamoyl methyl-2-oxopiperazine-1-acetic acid benzyl ester hydrochloride, 1.1 g of triethylamine and 30 mg of 4-dimethylaminopyridine. The mixture was stirred for 12 hours at room temperature. The reaction mixture was concentrated under reduced pressure. The concentrate was dissolved in methylene chloride, which was washed with a 5% aqueous solution of potassium hydrogensulfate then with a 10% aqueous solution of sodium hydrogencarbonate, followed by concentration under reduced pressure to give an oily product. The oily product was dissolved in 10 ml of 2N HCl-dioxane, which was left standing for one hour at room temperature. The reaction mixture was concentrated under reduced pressure and then processed with ether to give 470 mg of the title compound as amorphous powder.

Elemental Analysis for $C_{17}H_{22}N_4O_5 \cdot HCl(398.85)$:
Calcd.: C, 51.19; H, 5.81; N, 14.05.
Found: C, 51.12; H, 5.99; N, 14.21.

WORKING EXAMPLE 22
(S)-3-Carbamoylmethyl-4-(trans-4-guanidinomethylcyclohexyl carbonylglycyl)-2-oxopiperazine-1-acetic acid hydrochloride To a mixture of 177 mg of trans-4-guanidinomethyl cyclohexane carboxylic acid hydrochloride, 135 mg of N-hydroxy-5-norbornene-2,3-dicarboximide and 2 ml of dimethylformamide was added 200 mg of dicyclohexyl carbodiimide. The mixture was stirred for one hour at 0° C., then for 2 hours at room temperature. Insolubles were filtered off. To the filtrate were added at 0° C. 300 mg of (S)-3-carbamoylmethyl-4-glycyl-2-oxopiperazine-1-acetic acid benzyl ester and 100 mg of triethylamine. The mixture was stirred for one hour at the same temperature then for one hour at room temperature, followed by concentration under reduced pressure to give a crude product. The crude product was dissolved in 30 ml of methanol, to which was added 100 mg of 10% palladium-carbon. The mixture was stirred for one hour in hydrogen streams. The catalyst was filtered off, and the filtrate was concentrated under reduced pressure to give a crude product. The crude product was subjected to a $C_{18}$—ODS column chromatography using a mixture of water and acetonitrile (97:3) as the eluent. Relevant fractions were combined and freeze-dried to afford 180 mg of the title compound as amorphous powder.

Specific optical rotation : $[\alpha]_D^{23} + 78.6°$ (C=0.25, MeOH)
Elemental Analysis for $C_{19}H_{31}N_7O_6 \cdot H_2O(507.97)$:
Calcd.: C, 44.93; H, 6.75; N, 19.30.
Found: C, 44.79; H, 7.04; N, 19.55.

WORKING EXAMPLE 23
(S)-3-Benzyloxycarbonylmethyl-2-oxopiperazine-1-acetic acid hydrochloride To a mixture of 8.6 g of (S)-4-t-butoxycarbonyl-1-t-butoxycarbonylmethyl-2-oxopiperazine-3-acetic acid, 2.5 g of benzyl alcohol, 50 mg of 4-dimethylaminopyridine and 30 ml of methylene chloride was added, at 0 C, 6.2 g of dicyclohexylcarbodiimide. The mixture was stirred for one hour. Insolubles were filtered off. To the filtrate was added 30 ml of trifluoroacetic acid, and the mixture was left standing for one hour. The reaction mixture was concentrated under reduced pressure. The concentrate was dissolved in a 4N HCl-ethyl acetate solution, and the solution was stirred for 30 minutes at room temperature, then subjected to evaporation to dryness. This procedure was repeated to give a crude product, which was processed with ether to afford 3.7 g of the title compound as amorphous powder.

Elemental Analysis for $C_{15}H_{18}N_2O_5 \cdot HCl(342.78)$:
Calcd.: C, 52.56; H, 5.59; N, 8.17.
Found: C, 52.37; H, 5.70; N, 8.00.

WORKING EXAMPLE 24
(S)-1-Carbamoylmethyl-2-oxopiperazine-3-acetic acid benzyl ester hydrochloride (S)-3-Benzyloxycarbonylmethyl-2-oxopiperazine-1-acetic acid hydrochloride (7.5 g) and sodium hydrogencarbonate (4.2 g) were dissolved in a mixture of 50 ml of dioxane and 50 ml of water. To the solution was added at 0° C. 5.5 g of di-t-butyl bicarbonate, and the mixture was stirred vigorously for one hour. The reaction mixture was concentrated to half of its original volume, and washed with ether then there was added 30 ml of a 10% aqueous solution of potassium hydrogen sulfate, followed by extraction with methylene chloride. The extract solution was dried over anhydrous magnesium sulfate, which was then concentrated to give a crude product. The crude product was dissolved in 50 ml of dioxane. To the solution was added 2.6 g of N-hydroxysuccinimide, then 5.2 g of dicyclohexylcarbodiimide. The mixture was stirred for one hour at room temperature. Insolubles were filtered off. To the filtrate was added 10 ml of 25% aqueous ammonia, and the mixture was stirred vigorously for one hour. The reaction mixture was concentrated under reduced pressure. The concentrate was dissolved in methylene chloride, and the solution was washed with water. The methylene chloride layer was dried over anhydrous magnesium sulfate, then concentrated under reduced pressure to give an oily product. The oily product was dissolved in 2N HCl-dioxane, and the solution was stirred for one hour. The reaction mixture was subjected to evaporation to dryness to give a crude product, which was recrystallized from ethanol to afford 2.0 g of the title compound as colorless prisms, m.p. 201°-202° C.

Specific optical rotation: $[\alpha]_{23}^D - 16.8°$ (C=1.8, MeOH)
Elemental Analysis for $C_{15}H_{19}N_3O_4 \cdot H_2O(359.81)$:
Calcd.: C, 50.07; H, 6.16; N, 11.68.
Found: C, 50.23; H, 6.16; N, 11.39.

WORKING EXAMPLE 25
(S)-1-Carbamoylmethyl-4-glycyl-2-oxopiperazine-3-acetic acid benzyl ester hydrochloride (S)-1-Carbamoylmethyl-2-oxopiperazine-3-acetic acid benzyl ester hydrochloride (900 mg) was subjected to substantially the same procedure as in Working Example 21 to afford 520 mg of the title compound as amorphous powder.

Elemental Analysis for $C_{17}H_{22}N_4O_5 \cdot HCl(398\ 85)$.
Calcd.: C, 51.19; H, 5.81; N, 14.05.
Found: C, 51.07; H, 6.03; N, 14.05.

WORKING EXAMPLE 26
(S)-1-Carbamoylmethyl-4-(trans-4-guanidinomethylcyclohexyl carbonylglycyl)-2-oxopiperazine-3-acetic acid hydrochloride (S)-1-Carbamoylmethyl-4-glycyl-2-oxopiperazine-3-acetic acid benzyl ester hydrochloride (500 mg) was subjected to substantially the same procedure as in Working Example 22 to afford 210 mg of the title compound as amorphous powder.

Specific optical rotation: $[\alpha]_D^{23} + 83.1°$ (C=0.28, MeOH)

Elemental Analysis for $C_{19}H_{31}N_7O_6 \cdot HCl \cdot \frac{1}{2} H_2O$ (498.97):
Calcd.: C, 45.74; H, 6.67; N, 19.65.
Found: C, 45.43; H, 6.45; N, 19.35.

WORKING EXAMPLE 27
N-(2,2-Diethoxyethyl)glycine benzyl ester

To a mixture of 10 g of aminoacetaldehyde diethyl acetal, 14 g of potassium carbonate and 50 ml of dimethylformamide was added dropwise, while stirring at room temperature, 13.8 g of benzyl ester of chloroacetic acid in the course of 30 minutes. The mixture was stirred for 12 hours. The reaction mixture was diluted with ether, washed with water and dried over anhydrous magnesium sulfate, followed by concentration under reduced pressure. The concentrate was purified by means of chromatography on silica gel using a mixture of n-hexane and ethyl acetate (3:2) as the eluent to afford 12.3 g of the title compound as a colorless oily product.

Elemental Analysis for $C_{15}H_{23}NO_4$ (281.35):
Calcd.: C, 64.04; H, 8.24; N, 4.98.
Found: C, 64.01; H, 8.33; N, 5.17.

WORKING EXAMPLE 28
N-(N-t-Butoxycarbonyl-O$^5$-benzyl-L-glutamyl)-N-(2,2-diethoxyethyl)glycine benzyl ester N-(2,2-Diethoxyethyl)glycine benzyl ester (7.0 g) and t-butoxycarbonyl-L-glutamic acid-γ-benzyl ester (8.4 g) were subjected to substantially the same procedure as in Working Example 2 to afford 5.5 g of the title compound as a colorless oily product.

Specific optical rotation: $[\alpha]_D^{23} - 19.2°$ (C=0.60, MeOH)

Elemental Analysis for $C_{32}H_{44}N_2O_9$ (600.71):
Calcd.: C, 63.98; H, 7.38; N, 4.66.
Found: C, 64.12; H, 7.50; N, 4.38.

WORKING EXAMPLE 29
(S)-4-t-Butoxycarbonyl-1-carboxymethyl-2-oxopiperazine-3-propionic acid N-(N-t-Butoxycarbonyl-O-benzyl-L-glutamyl)-N-(2,2-diethoxyethyl)glycine benzyl ester (5.5 g) was subjected to substantially the same procedure as in Working Example 3 to afford the title compound as a colorless oily product.

Elemental Analysis for $C_{14}H_{22}N_2O_7$ (330.34):
Calcd.: C, 50.90; H, 6.71; N, 8.48.
Found: C, 50.67; H, 6.72; N, 8.53.

WORKING EXAMPLE 30
(S)-1-Benzyloxycarbonylmethyl-2-oxopiperazine-3-propionic acid benzyl ester hydrochloride A mixture of 3.0 g of (S)-4-t-butoxycarbonyl-1-carboxymethyl-2-oxopiperazine-3-propionic acid, 3.4 g of benzyl bromide, 3.0 g of potassium hydrogencarbonate and 15 ml of dimethylformamide was stirred for 5 hours at room temperature. The reaction mixture was poured into ice-water, which was subjected to extraction with ethyl acetate. The extract solution was dried over anhydrous magnesium sulfate, which was concentrated under reduced pressure to give a crude product. The crude product was dissolved in 2N HCl-ethyl acetate solution. The solution was left standing for one hour at room temperature. The reaction mixture was subjected to evaporation to dryness. The residue was processed with ether to afford 2.9 g of the title compound as amorphous powder.

Specific optical rotation: $[\alpha]_D^{23} - 15.0°$ (C=0.77, MeOH)

Elemental Analysis for $C_{23}H_{26}N_2O_5 \cdot HCl$ (446.93):
Calcd.: C, 61.81; H, 6.09; N, 6.27.
Found: C, 61.72; H, 6.35; N, 6.51.

WORKING EXAMPLE 31
(S)-1-Benzyloxycarbonylmethyl-4-glycyl-2-oxopiperazine-3-propionic acid benzyl ester hydrochloride (S)-1-Benzyloxycarbonyl-2-oxopiperazine-3-propionic acid benzyl ester hydrochloride (1.7 g) was subjected to substantially the same procedure as in Working Example 21 to afford 490 mg of the title compound as amorphous powder.

Elemental Analysis for $C_{25}H_{29}N_3O_6 \cdot HCl$ (503.98):
Calcd.: C, 59.58; H, 6.00; N, 8.34.
Found: C, 59.46; H, 6.23; N, 8.33.

WORKING EXAMPLE 32
(S)-1-Carboxylmethyl-4-(trans-4-guanidinomethylcyclohexyl carbonylglycyl)-2-oxopiperazine-3-propionic acid hydrochloride (S)-1-Benzyloxycarbonylmethyl-4-glycyl-2-oxopiperazine-3-propionic acid benzyl ester hydrochloride (490 mg) was subjected to substantially the same procedure as in Working Example 22 to afford 220 mg of the title compound as amorphous powder.

Specific optical rotation: $[\alpha]_D^{23} + 50.5°$ (C=0.25, MeOH)

Elemental Analysis for $C_{20}H_{32}N_6O_7 \cdot HCl \cdot 5/2 H_2O$ (550.01):
Calcd.: C, 43.68; H, 6.96; N, 15.28.
Found: C, 43.81; H, 6.95; N, 15.37.

WORKING EXAMPLE 33
2-Oxopiperazine-1-acetic acid benzyl ester hydrochloride

In a mixture of 100 ml of water and 100 ml of dioxane were dissolved 13.7 g of 2-oxopiperazine hydrochloride and 16.8 g of sodium hydrogencarbonate. To the solution was added 22.0 g of di-t-butyl bicarbonate, and the mixture was stirred vigorously for 3 hours at 0° C. The reaction mixture was concentrated to half of its original volume, which was subjected to extraction with methylene chloride. The extract solution was dried over anhydrous magnesium sulfate, followed by concentration under reduced pressure to give a crude product. The crude product was dissolved in 50 ml of acetonitrile, to which were added 18.5 g of benzyl ester of chloroacetic acid and 16.0 g of cesium fluoride. The mixture was stirred for 2 hours at 50° C. and then left standing for cooling. The reaction mixture was subjected to evaporation to dryness, and the residue was dissolved in methylene chloride, which was washed with water. The methylene chloride layer was dried over anhydrous magnesium sulfate and then concentrated under reduced pressure to give a crude product. The crude product was dissolved in 2N HCl-dioxane solution. The solution was left standing for 2 hours at room temperature. Resulting crystalline precipitates were collected by filtration and recrystallized from ethanol to afford 9.9 g of the title compound as colorless prisms, m.p.165° C.

Elemental Analysis for $C_{13}H_{16}N_2O_3 \cdot HCl(284.74)$:
Calcd.: C, 54.84; H, 6.02; N, 9.84.
Found: C, 54.97; H, 5.81; N, 9.88.

WORKING EXAMPLE 34
4-Glycyl-2-oxopiperazine-1-acetic acid benzyl ester hydrochloride 2-Oxopiperazine-1-acetic acid benzyl ester hydrochloride (2 g) was subjected to substantially the same procedure as in Working Example 21 to afford 1.2 g of the title compound as amorphous powder.

Elemental Analysis for $C_{15}H_{18}N_3O_4 \cdot HCl(341.79)$:
Calcd.: C, 52.71; H, 5.90; N, 12.29.
Found: C, 52.50; H, 6.11; N, 12.58.

WORKING EXAMPLE 35
4-(trans-4-Guanidinomethylcyclohexylcarbonyl-glycyl)-2-oxopiperazine-1-acetic acid hydrochloride 4-Glycyl-2-oxopiperazine-1-acetic acid benzyl ester hydrochloride (450 mg) was subjected to substantially the same procedure as in Working Example 22 to afford 190 mg of the title compound as amorphous powder.

Elemental Analysis for $C_{17}H_{28}N_6O_5 \cdot \frac{1}{2}H_2O(441.91)$:
Calcd.: C, 46.21; H, 6.84; N, 19.02.
Found: C, 46.41; H, 7.19; N, 18.79.

WORKING EXAMPLE 36
4-L-Phenylalanyl-2-oxopiperazine-1-acetic acid benzyl ester hydrochloride 2-Oxopiperazine-1-acetic acid benzyl ester hydrochloride (2 g) and N-t-butoxycarbonyl-L-phenylalanine (5.6 g) were subjected to substantially the same procedure as in Working Example 21 to afford 1.5 g of the title compound as amorphous powder.

Elemental Analysis for $C_{22}H_{25}N_3O_4 \cdot HCl(431.92)$:
Calcd.: C, 61.18; H, 6.07; N, 9.73.
Found: C, 60.90; H, 6.27; N, 9.70.

WORKING EXAMPLE 37
4-(trans-4-Guanidinomethylcyclohexylcarbonyl-L-phenylalanyl)-2-oxopiperazine-1-acetic acid hydrochloride 4-L-Phenylalanyl-2-oxopiperazine-1-acetic acid benzyl ester hydrochloride (400 mg) was subjected to substantially the same procedure as in Working Example 22 to afford 97 mg of the title compound as amorphous powder.

Optical rotation: $[\alpha]_D^{23} +3.3$ (C=0.25, MeOH)
Elemental Analysis for $C_{24}H_{34}N_6O_5 \cdot HCl \cdot 3/2 H_2O 550.05)$:
Calcd.: C, 52.41; H, 6.96; N, 15.28.
Found: C, 52.64; H, 7.20; N, 15.27.

WORKING EXAMPLE 38
(S)-4-(1-Amidinopiperidin-4-ylcarbonylglycyl)-2-oxo piperazine-1,3-diacetic acid hydrochloride In substantially the same procedure as in Working Example 5, (S)-4-glycyl-2-oxopiperazine-1,3-diacetic acid di-t-butyl ester was subjected to condensation with N-amidinopiperidine-4-carboxylic acid hydrochloride to afford amorphous powder.

Elemental Analysis for $C_{17}H_{26}N_6O_7 \cdot HCl(462.89)$:
Calcd.: C, 44.11; H, 5.88; N, 18.16.
Found: C, 43.84; H, 6.02; N, 18.10.

WORKING EXAMPLE 39
(S)-4-(4-Amidinobenzoylglycyl)-2-oxopiperazine-1,3-diacetic acid To a mixture of 320 mg of 4-amidinobenzoic acid hydrochloride, 286 mg of N-hydroxy-5-norbornene-2,3-dicarboximide and 5 ml of dimethylformamide was added 412 mg of dicyclohexylcarbodiimide. The mixture was stirred for one hour at 0° C., then for 2 hours at room temperature. Insolubles were filtered off, and the filtrate was cooled with ice and there were added 500 mg of (S)-4-glycyl-2-oxopiperazine-1,3-diacetic acid di-t-butyl ester hydrochloride, then 150 mg of triethylamine. The mixture was stirred for one hour at the same temperature range. The reaction mixture was concentrated under reduced pressure to leave an oily product, which was dissolved in 5 ml of methylene chloride. To the solution was added 5 ml of trifluoroacetic acid at 0° C. and it was warmed up to room temperature, then stirred for one hour. The reaction mixture was concentrated to give a crude product, which was converted to the hydrochloride with 1N HCl, followed by subjecting to $C_{18}$—ODS column (water-:acetonitrile=98:2). The eluate was freeze-dried to afford 200 mg of the title compound as amorphous powder.

Specific optical rotation $[\alpha]_D^{20} +83.0°$ (C=0.995, $H_2O$).

Elemental Analysis for $C_{18}H_{21}N_5O_7 \cdot HCl \cdot 2H_2O$:
Calcd.: C, 43.95; H, 5.33; N, 14.24.
Found: C, 44.26; H, 5.37; N, 13.90.

In 50 ml of water was dissolved 3.9 g of the hydrochloride thus obtained. The solution was subjected to column chromatography on Amberlite XAD-2 (eluent: $H_2O \rightarrow 10\%$ acetonitrile). The object fraction was freeze-dried to give (S)-4-(4-amidinobenzoylglycyl)-2-oxopiperazine- 1,3-diacetic acid as colorless powder. This product (1.13 g) was dissolved in 10 ml of water, to which was added 30 ml of ethanol, and the mixture was left standing. Resulting precipitates were collected by filtration to afford 0.46 g of (S)-4-(4-amidinobenzoylglycyl)-2-oxopiperazine-1,3-acetic acid as colorless crystals, m.p. 254° to 258° C. (decomp.)

Specific optical rotation $[\alpha]_D^{20} +90$ 1° (C=0.995, $H_2O$).

Elemental Analysis for $C_{18}H_{21}N_5O_7 \cdot \frac{1}{2}H_2O$:
Calcd.: C, 50.47; H, 5.18; N, 16.35.
Found: C, 50.11; H, 5.19; N, 16.13.

In substantially the same manner as in Working Example 39, the following compounds were synthesized.

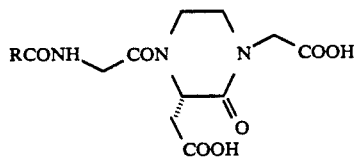

| Working Example | RCO— | Rational Formula | Found (Calcd.) | $[\alpha]_D^{23}$ (C, H$_2$O) |
|---|---|---|---|---|
| 40 | H$_2$N-C(=HN)-NH-(CH$_2$)$_3$-CH(NH$_2$)-CO— | C$_{16}$H$_{27}$N$_7$O$_7$.HCl | C, 41.01; H, 6.30; N, 20.93 (C, 41.25; H, 6.06; N, 21.04) | +61.0° (0.1) |
| 41 | H$_2$N-C(=HN)-NH-C$_6$H$_4$-CO— | C$_{18}$H$_{22}$N$_6$O$_7$.HCl | C, 45.99; H, 5.13; N, 17.65 (C, 45.91; H, 4.92; N, 17.85) | +80.4° (0.2) |
| 42 | (CH$_3$)$_2$N-C(=HN)-NH-C$_6$H$_4$-CO— | C$_{20}$H$_{26}$N$_6$O$_7$.HCl.H$_2$O | C, 46.19; H, 5.88; N, 16.07 (C, 46.47; H, 5.65; N, 16.26) | +95.6° (0.15) |
| 43 | H$_2$N-C(=HN)-NH-(thiazolyl)-CO— | C$_{15}$H$_{19}$N$_7$O$_7$S.HCl | C, 37.56; H, 4.48; N, 20.24 (C, 37.70; H, 4.22; N, 20.52) | +66.4° (0.2) |
| 44 | H$_2$N-C(=HN)-C$_6$H$_4$-CO— | C$_{18}$H$_{21}$N$_5$O$_7$HCl | C, 47.19; H, 4.86; N, 15.25 (C, 47.43; H, 4.86; N, 15.36) | +73.7° (0.15) |
| 45 | H$_2$N-C(=HN)-C$_6$H$_4$-CH$_2$CO— | C$_{19}$H$_{23}$N$_5$O$_7$.HCl.H$_2$O | C, 46.47; H, 5.39; N, 14.08 (C, 46.77; H, 5.37; N, 14.35) | +92.6° (0.3) |

WORKING EXAMPLE 46
(S)-4-[4-(2-Aminoethyl)benzoylglycyl]-2-oxopiperazine-1,3-di-acetic acid trifluoroacetate In 3 ml of dimethylformamide were dissolved 292 mg of 4-(2-t-butoxycarbonylaminoethyl)benzoic acid and 500 mg of (S)-4-glycyl-2-oxopiperazine-1,3-diacetic acid di-t-butyl ester hydrochloride obtained in Working Example 4. The solution was cooled with ice and there were added dropwise 330 mg of diethyl cyanophosphonate then 303 mg of triethylamine. The mixture was stirred for 2 hours. The reaction mixture was diluted with ethyl acetate, which was poured into ice-water. The organic layer was washed with a 5% aqueous solution of potassium hydrogensulfate and a saturated aqueous solution of sodium hydrogencarbonate and was dried over anhydrous magnesium sulfate, followed by concentration under reduced pressure. The concentrate was dissolved in 5 ml of methylene chloride, to which was added dropwise 5 ml of trifluoroacetic acid at 0° C. The mixture was warmed up to room temperature and stirred for one hour. The reaction mixture was concentrated under reduced pressure to give a crude product, which was subjected to column chromatography on C$_{18}$—ODS (H$_2$O-acetonitrile=97:3). The eluate was freeze-dried to afford 350 mg of the title compound as amorphous powder.

Specific optical rotation $[\alpha]_D^{23}$ +88.7° (C=0.2, H$_2$O)
Elemental Analysis for C$_{19}$H$_{24}$N$_4$O$_7$.CF$_3$CO$_2$H:
Calcd.: C, 47.19; H, 4.71; N, 10.48.
Found: C, 47.01; H, 4.99; N, 10.45.

In substantially the same procedure as in Working Example 46, the following compounds were synthesized.

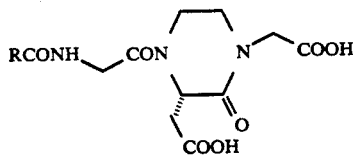

| Working Example | RCO— | Rational Formula | Found (Calcd.) | $[\alpha]_D^{20}$ (C, H$_2$O) |
|---|---|---|---|---|
| 47 | H$_2$NCH$_2$—〔benzene〕—CO— | C$_{18}$H$_{22}$N$_4$O$_7$·CF$_3$CO$_2$H | C, 45.95; H, 4.63; N, 10.49 (C, 46.16; H, 4.45; N, 10.77) | +90.4° (0.25) |
| 48 | H$_2$N—(CH$_2$)$_3$—〔benzene〕—CO— | C$_{20}$H$_{26}$N$_4$O$_7$·HCl | C, 51.11; H, 5.57; N, 12.08 (C, 51.01; H, 5.78; N, 11.90) | +99.9° (0.2) |

WORKING EXAMPLE 49

4-(N-Benzyloxycarbonyl-L-prolyl)-2-oxopiperazine-1,3-diacetic acid di-t-butyl ester In 20 ml of dimethylformamide was dissolved 1.25 g of carbobenzyloxy-L-proline. The solution was cooled to −10° C., then there was added 810 mg of phosgene iminium chloride, and the mixture was stirred for 2 hours. To the mixture were added dropwise 5 ml of dimethylformamide containing 1.8 g of (S)-2-oxopiperazine-1,3-diacetic acid di-t-butyl ester synthesized in Working Example 3, then 2 ml of triethylamine. The mixture was stirred for one hour. The reaction mixture was diluted with ethyl acetate and was poured into ice-water. The organic layer was washed with a 5% potassium hydrogensulfate and a saturated aqueous solution of sodium hydrogenphosphate. The extract solution was dried over anhydrous magnesium sulfate and was concentrated under reduced pressure to give a crude product. The crude product was purified by s silica gel chromatography (ethyl acetate) to afford 1.0 g of the title compound as amorphous powder.

Specific optical rotation $[\alpha]_D^{23}$ +41.0° (C=1.0, MeOH)

Elemental Analysis for C$_{29}$H$_{41}$N$_3$O$_8$:
Calcd.: C, 62.24; H, 7.38; N, 7.51.
Found: C, 62.01; H, 7.59; N, 7.50.

WORKING EXAMPLE 50

4-(4-Guanidinobenzoylprolyl)-2-oxopiperazine-1,3-diacetic acid hydrochloride

A mixture of 560 mg of 4-(N-benzyloxycarbonyl)-L-prolyl-2-oxopiperazine-1,3-diacetic acid di-t-butyl ester and 10 ml of methanol containing 100 mg of 10% palladium-carbon was stirred for one hour at room temperature in a hydrogen streams. The catalyst was filtered off, and the filtrate was concentrated. The resulting oily product was dissolved in 2 ml of dimethylformamide. To the solution were added 216 mg of 4-guanidinobenzoic acid hydrochloride, 180 mg of N-hydroxy-5-norbornene-2,3-dicarboximide, then 206 mg of dicyclohexylcarbodiimide. The mixture was stirred for one hour. Insolubles were filtered off, and the filtrate was concentrated to give an oily product. The oily product was dissolved in 10 ml of trifluoroacetic acid, and the solution was left standing for one hour at room temperature. The reaction mixture was concentrated to give a crude product, which was converted into hydrochloride with 1N HCl. The hydrochloride was subjected to a C$_{18}$—ODS column (H$_2$O-acetonitrile=95:5). The eluate was freeze-dried to afford 210 mg of the title compound as amorphous powder.

Specific optical rotation $[\alpha]_D^{23}$ +24.6° (C=0.2, H$_2$O).
Elemental Analysis for C$_{21}$H$_{26}$N$_6$O$_7$·HCl:
Calcd.: C, 49.37; H, 5.33; N, 16.45.
Found: C, 49.35; H, 5.29; N, 16.54.

WORKING EXAMPLE 51

4-(4-Guanidinobenzoylsarcosyl)-2-oxopiperazine-1,3-diacetic acid hydrochloride

To 5 ml of dimethylformamide containing 800 mg of 4-sarcosyl-2-oxopiperazine-1,3-diacetic acid di-t-butyl ester obtained in Working Example 11 and 300 mg of triethylamine was added dropwise at 0° C., taking 5 minutes, 1 ml of dimethylformamide containing 400 mg of 4-guanidinobenzoyl chloride hydrochloride. The reaction mixture was concentrated under reduced pressure to give an oily product. The oily product was dissolved in 5 ml of trifluoroacetic acid and was left standing for one hour. The reaction mixture was concentrated under reduced pressure to give a crude product, which was converted into hydrochloride with 1N HCl, followed by subjecting the hydrochloride to C$_{18}$—ODS column (H$_2$O-acetonitrile=97:3). The eluate was freeze-dried to afford 250 mg of the title compound as amorphous powder.

Specific optical rotation $[\alpha]_D^{23}$ +61.5° (C=0.3, H$_2$O).
Elemental Analysis for C$_{19}$H$_{24}$N$_6$O$_7$·HCl:
Calcd.: C, 47.06; H, 5.20; N, 17.33.
Found: C, 47.29; H, 5.25; N, 17.09.

WORKING EXAMPLE 52

N-(2,2-Diethoxyethyl)-L-phenylalanine t-butyl ester

A mixture of 2.58 g of L-phenylalanine t-butyl ester hydrochloride, 2.76 g of potassium carbonate, 0.1 g of sodium iodide, 2.2 g of 2-bromo-1,1-diethoxyethane and 30 ml of N,N-dimethylformamide was stirred for 24 hours at 100° C. The reaction mixture was poured into ice-water, which was subjected to extraction with hexane. The organic layer was washed with water, dried over anhydrous magnesium sulfate, then concentrated under reduced pressure. The concentrate was purified by means of a silica gel column chromatography (eluent: ethyl acetate-hexane=1:4→1:2) to afford 2.2 g of the title compound as a pale yellow oily product.

Specific optical rotation $[\alpha]_D^{23}+10.0°$ (C=1.045, MeOH).

WORKING EXAMPLE 53
(S,S)-2-[3-t-Butoxycarbonylmethyl-2-oxopiperazine-1-yl]-2-benzyl acetic acid t-butyl ester oxalate N-(2,2-Diethoxyethyl)-L-phenylalanine t-butyl ester obtained in Working Example 52 was subjected to condensation, in substantially the same manner as in Working Example 2, with N-carbobenzyloxy-L-aspartic acid t-butyl ester. The condensate was subjected to ring-closure and reduction, in substantially the same manner as in Working Example 3, to give oxalate. The oxalate was crystallized from ethyl acetate to afford the title compound as colorless crystals, m.p.180 to 181° C. (decomp.).

Specific optical rotation $[\alpha]_D^{20}-68.3°$ (C=0.205, MeOH)

Elemental Analysis for $C_{25}H_{36}N_2O_9$:
Calcd.: C, 59.04; H, 7.13; N, 5.51.
Found: C, 58.93; H, 7.08; N, 5.51.

WORKING EXAMPLE 54
(S,S)-2-[4-(4-Amidinobenzoylglycyl)-3-carboxymethyl-2-oxopiperazine-1-yl]-2-benzyl acetic acid hydrochloride To 5 ml of dimethylformamide containing 420 mg of carbobenzyloxy glycine was added, at room temperature, 210 mg of dicyclohexyl carbodiimide. The mixture was stirred for one hour. Insolubles were filtered off. To the filtrate were added 420 mg of (S,S)-2-[3-t-butoxycarbonylmethyl-2-oxopiperazine-1-yl]-2-benzyl acetic acid t-butyl ester obtained in Working Example 53 and 500 mg of triethylamine. The mixture was stirred for 3 hours at room temperature. The reaction mixture was diluted with ethyl acetate and was washed with a 5% aqueous solution of potassium hydrogensulfate, then with a 10% aqueous solution of sodium hydrogencarbonate, followed by drying over anhydrous magnesium sulfate and concentration under reduced pressure to leave an oily product. The oily product was dissolved in 10 ml of methanol, to which was added 10% palladium-carbon. The mixture was stirred for one hour at room temperature in a hydrogen stream. The catalyst filtered off, then the filtrate was concentrated to give an oily product. The oily product and 200 mg of 4-amidinobenzoic acid hydrochloride were subjected to substantially the same procedure as in Working Example 39 to afford 100 mg of the title compound as amorphous powder.

Specific optical rotation $[\alpha]_D^{23}-30.9°$ (C=0.2, H₂O)
Elemental Analysis for $C_{25}H_{27}N_5O_7 \cdot HCl$:
Calcd.: C, 55.00; H, 5.17; N, 12.83.
Found: C, 54.72 H, 5.47; N, 12.86.

WORKING EXAMPLE 55
4-(4-Amidinobenzoylglycyl)-2-oxopiperazine-1-acetic acid

4-Amidinobenzoic acid hydrochloride (200 mg) and 340 mg of 4-glycyl-2-oxopiperazine-1-acetic acid benzyl ester obtained in Working Example 34 were subjected to substantially the same procedure as in Working Example 22 to afford 150 mg of the title compound as colorless prisms, m.p.255° C. (decomp.).

Elemental Analysis for $C_{16}H_{19}N_5O_5 \cdot 3/2H_2O$:
Calcd.: C, 49.48; H, 5.71; N, 18.03.
Found: C, 49.57; H, 5.51; N, 17.78.

WORKING EXAMPLE 56
(S)-4-Glycyl-1-methoxycarbonylmethyl-2-oxopiperazine-3-acetic acid t-butyl ester hydrochloride A mixture of 4.1 g of N-(2,2-diethoxyethyl)glycyl methyl ester and 6.4 g of N-benzyloxycarbonyl-L-aspartic acid-β-t-butyl ester was subjected substantially the same procedures as in Working Examples 2, 3 and 4 to afford 2.9 g of the title compound as amorphous powder.

Specific optical rotation $[\alpha]_D^{23}+89.7°$ (C=0.2, MeOH)

Elemental Analysis for $C_{15}H_{25}N_3O_6 \cdot HCl$:
Calcd.: C, 47.43; H, 6.90; N, 11.06.
Found: C, 47.45; H, 7.13; N, 10.88.

WORKING EXAMPLE 57
(S)-4-(4-Amidinobenzoylglycyl)-1-methoxycarbonylmethyl-2-oxopiperazine-3-acetic acid hydrochloride A mixture of 380 mg of (S)-4-glycyl-1-methoxycarbonylmethyl-2-oxopiperazine-3-acetic acid t-butyl ester obtained in Working Example 56 and 200 mg of 4-amidinobenzoic acid was subjected to substantially the same procedure as in Working Example 39 to afford 210 mg of the title compound as amorphous powder.

Specific optical rotation $[\alpha]_D^{23}+91.4°$ (C=0.2, H₂O).
Elemental Analysis for $C_{19}H_{23}N_5O_7 \cdot HCl \cdot \frac{1}{2}H_2O$:
Calcd.: C, 47.65; H, 5.26; N, 14.62.
Found: C, 47.82; H, 5.32; N, 14.53.

WORKING EXAMPLE 58
(S)-4-(N-Benzyloxycarbonylglycyl)-3-methoxycarbonylmethyl-2-oxopiperazine-1-acetic acid t-butyl ester To 30 ml of methylene chloride containing 1.9 g of (2,2-diethoxyethyl)glycine t-butyl ester and 2.2 g of N-benzyloxycarbonyl-L-aspartic acid-β-methyl ester was added, at room temperature, 1.9 g of 1-ethyl-3-(3-dimethylaminopropyl) carbodiimide hydrochloride. The mixture was stirred for one hour. The reaction mixture was washed with a 5% aqueous solution of potassium hydrogensulfate, then with a 10% aqueous solution of sodium hydrogencarbonate and dried over anhydrous magnesium sulfate, followed by concentration under reduced pressure. The resultant oily product was dissolved in 200 ml of toluene, to which was added 190 mg of p-toluenesulfonic acid. The mixture was stirred for one hour at 50° C. The reaction mixture was washed with a saturated aqueous solution of sodium hydrogencarbonate, dried over anhydrous magnesium sulfate and concentrated under reduced pressure. The resultant oily product was dissolved in 30 ml of dimethylformamide. To the solution were added 1.6 g of carbobenzyloxy glycine and, then, 1.9 g of 1-(3-dimethylaminopropyl)-3-ethyl carbodiimide hydrochloride. The mixture was stirred for 3 hours at room temperature. The reaction mixture was washed with a 5% aqueous solution of potassium hydrogensulfate, then with a 10% aqueous solution of sodium hydrogencarbonate, followed by drying over anhydrous magnesium sulfate and concentration under reduced pressure to give a crude product. The crude product was purified by means of a silica gel chromatography (ethyl acetate) to afford 2.4 g of the title compound as colorless powder.

Specific optical rotation $[\alpha]_D^{23}+75.7°$ (C=1.0, MeOH).

WORKING EXAMPLE 59
(S)-4-(4-Amidinobenzoylglycyl)-3-methoxycarbonyl-methyl-2-oxopiperazine-1-acetic acid hydrochloride In 10 ml of methanol was dissolved 480 mg of (S)-4-(N-benzyloxycarbonylglycyl)-3-methoxycarbonyl-methyl-2-oxo-piperazin-1-acetic acid t-butyl ester obtained in Working Example 58. To the solution was added 100 mg of 10% palladium-carbon, and the mixture was stirred for one hour at room temperature in a hydrogen streams. The catalyst was filtered off, and the filtrate was concentrated to give an oily product, which was dissolved in 5 ml of dimethylformamide. To the solution were added 200 mg of 4-amidinobenzoic acid hydrochloride, then 200 mg of (1-(3-dimethylamino-propyl)-3-ethyl carbodiimide hydrochloride. The mixture was stirred for one hour at room temperature. The reaction mixture was diluted with ethyl acetate, washed with a 5% aqueous solution of potassium hydrogensulfate, then a 10% aqueous solution of sodium hydrogencarbonate, followed by drying over anhydrous magnesium sulfate and concentration under reduced pressure to leave an oily product. The oily product was dissolved in 5 ml of methylene chloride. To the solution was added 5 ml of trifluoroacetic acid, and the mixture was stirred for one hour at room temperature. The reaction mixture was concentrate to give a crude product, which was made into hydrochloride with 1N HCl, followed by purification by means of a $C_{18}$—ODS column to afford 250 mg of the title compound as colorless powder.

Specific optical rotation $[\alpha]_D^{23}+90.0°$ (C=0.2, $H_2O$)
Elemental Analysis for $C_{19}H_{23}N_5O_7 \cdot HCl$:
Calcd.: C, 48.57; H, 5.15; N, 14.90.
Found: C, 48.71; H, 5.45; N, 14.70.

WORKING EXAMPLE 60
(S)-4-[4-(2-Aminoethyl)benzoylglycyl]-3-methoxycarbonyl methyl-2-oxopiperazine-1-acetic acid hydrochloride In 10 ml of methanol was dissolved 500 mg of (S)-4-(N-benzyloxycarbonylglycyl)-3-methoxycarbonyl-methyl-2-oxo-piperazine-1-acetic acid t-butyl ester obtained in Working Example 58. To the solution was added 100 mg of 10% palladium-carbon, and the mixture was stirred for one hour at room temperature. The catalyst was filtered off, and the filtrate was concentrated to give an oily product. The oily product was dissolved in 5 ml of dimethylformamide, to which was added 290 mg of 4-(2-t-butoxycarbonylaminoethyl)benzoic acid. The mixture was cooled with ice, to which were added dropwise 240 mg of diethyl cyanophosphonate then 300 mg of triethylamine. The mixture was stirred for one hour. The reaction mixture was diluted with ethyl acetate, washed with a 5% aqueous solution of potassium hydrogensulfate, then with a 10% aqueous solution of sodium hydrogencarbonate, dried over anhydrous magnesium sulfate, then concentrated under reduced pressure. The resultant oily product was dissolved in 5 ml of methylene chloride. To the solution was added 5 ml of trifluoroacetic acid, and the mixture was stirred for one hour at room temperature. The reaction mixture was concentrated to give a crude product, which was made into hydrochloride with 1N HCl, followed by purification by means of $C_{18}$—ODS column to afford 300 mg of the title compound as colorless powder.

Specific rotatory powder $[\alpha]_D^{23}+81.5°$ (C=0.2, $H_2O$).
Elemental Analysis for $C_{20}H_{26}N_4O_7 \cdot HCl$:
Calcd.: C, 51.01; H, 5.78; N, 11.90.
Found: C, 51.09; H, 5.98; N, 11.95.

WORKING EXAMPLE 61
(S)-4-(4-Amidinobenzoylglycyl)-3-benzyl-2-oxopiperazine-1-acetic acid (S)-4-Glycyl-3-benzyl-2-oxopiperazine-1-acetic acid t-butyl ester (400 mg) obtained in Working Example 15 and 200 mg of 4-amidinobenzoic acid hydrochloride were subjected to substantially the same procedure as in Working Example 39 to afford 100 mg of the title compound as colorless crystals, m.p.290°-296° C. (decomp.).

Specific optical rotation $[\alpha]_D^{23}+96.9°$ (C=0.1, 1N HCl).

WORKING EXAMPLE 62
(S)-3-Benzyl-4-(N-carbobenzyloxyglycyl)-2-oxopiperazine-1-acetic acid pivaloyloxy methyl ester To 5 ml of dimethylformamide containing 680 mg of (S)-3-benzyl-2-oxopiperazine-1-acetic acid t-butyl ester hydrochloride obtained in Working Example 14 and 420 mg of carbobenzyloxyglycine was added, at room temperature, 400 mg of 1-ethyl-3-(3-dimethylaminopropyl) carbodiimide hydrochloride, and the mixture was stirred for one hour. The reaction mixture was diluted with ethyl acetate, washed with a 5% aqueous solution of potassium hydrogensulfate, then with a 10% aqueous solution of sodium hydrogencarbonate, dried over anhydrous magnesium sulfate, and concentrated under reduced pressure. The resultant oily product was dissolved in trifluoroacetic acid, and the solution was left standing for one hour at room temperature. The reaction mixture was concentrated to give an oily product, which was dissolved in 5 ml of dimethylformamide. To the solution were added 450 mg of pivaloyloxymethyl chloride, 770 mg of diisopropylethylamine and 520 mg of sodium iodide. The mixture was stirred for 6 hours at room temperature. The reaction mixture was concentrated under reduced pressure. The concentrate was dissolved in methylene chloride, washed with water, dried over anhydrous magnesium sulfate, and concentrated under reduced pressure. Resultant crude product was purified by means of a silica gel chromatography (methylene chloride:ethyl acetate=4:6) to afford 880 mg of the title compound as a colorless foamy product.

Specific optical rotation $[\alpha]_D^{23}+50.1°$ (C=0.5, MeOH)

WORKING EXAMPLE 63
(S)-4-(4-Amidinobenzoylglycyl)-3-benzyl-2-oxopiperazine-1-acetic acid pivaloyloxy methyl ester hydrochloride In 10 ml of methanol was dissolved 550 mg of (S)-3-benzyl-4-(N-carbobenzyloxyglycyl)-2-oxopiperazine-1-acetic acid pivaloyloxy methyl ester. To the solution was added 100 mg of 10% palladium-carbon, and the mixture was stirred for one hour at room temperature. The catalyst was filtered off, and the filtrate was concentrated to give an oily product, which was dissolved in 5 ml of dimethylformamide. To the solution were added 200 mg of 4-amidinobenzoic acid hydrochloride, 180 mg of N-hydroxy-5-norbornene-2,3-dicarboximide and 210 mg of dicyclohexylcarbodiimide. The mixture was stirred for one hour at room temperature. The reaction mixture was concentrated under reduced pressure to give a crude product, which was purified by means of $C_{18}$—ODS column to afford 120 mg of the title compound as colorless powder.

Specific optical rotation $[\alpha]_D^{23}+73.1°$ (C=0.15, $H_2O$).

Elemental Analysis for $C_{29}H_{35}N_5O_7.HCl.H_2O$:
Calcd.: C, 56.17; H, 6.18; N, 11.29.
Found: C, 56.05; H, 6.35; N, 11.20.

WORKING EXAMPLE 64
(S)-4-Glycyl-3-(1-methylpropyl)-2-oxopiperazine-1-acetic acid t-butyl ester hydrochloride N-(2,2-Diethoxyethyl)glycine t-butyl ester (2.5 g) and 2.65 g of carbobenzyloxyisoleucine were subjected to substantially the same procedures as in Working Examples 2, 3 and 4 to afford 3.0 g of the title compound as colorless powder.

Specific optical rotation $[\alpha]_D^{23}+42.9°$ (C=1.2, MeOH).

WORKING EXAMPLE 65
(S)-4-(4-Guanidinobenzoylglycyl)-3-(1-methylpropyl)-2-oxopiperazine-1-acetic acid hydrochloride (S)-4-Glycyl-3-(1-methylpropyl)-2-oxopiperazine-1-acetic acid t-butyl ester hydrochloride obtained in Working Example 64 (364 mg) and 215 mg of 4-guanidino benzoic acid hydrochloride were subjected to substantially the same procedure as in Working Example 39 to afford 190 mg of the title compound as colorless powder.

Specific optical rotation $[\alpha]_D^{23}+25.7°$ (C=0.2, $H_2O$)
Elemental Analysis for $C_{20}H_{28}N_6O_5.HCl$:
Calcd.: C, 51.23; H, 6.23; N, 17.92.
Found: C, 51.09; H, 6.48; N, 17.71.

WORKING EXAMPLE 66
(S)-4-(4-Amidinobenzoylglycyl)-1-carboxymethyl-2-oxopiperazine-3-propionic acid (S)-1-Benzyloxycarbonylmethyl-4-glycyl-2-oxopiperazine-3-propionic acid benzyl ester hydrochloride (490 mg) obtained in Working Example 31 and 200 mg of 4-amidinobenzoic acid hydrochloride were subjected to substantially the same procedure as in Working Example 32 to afford 140 mg of the title compound as colorless prisms, m.p.235°–241° C.

Specific optical rotation $[\alpha]_D^{23}+66.6°$ (C=0.3, $H_2O$).
Elemental Analysis for $C_{19}H_{23}N_5O_7.\frac{1}{2}H_2O$:
Calcd.: C, 51.58; H, 5.47; N, 15.83.
Found: C, 51.63; H, 5.86; N, 16.01.

WORKING EXAMPLE 67
N-(2,2-Diethoxyethyl)-L-alanine t-butyl ester

L-Alanine-t-butyl ester was allowed to react with 2-bromo-1,1-diethoxyethane in substantially the same manner as in Working Example 52 to afford the title compound as a yellowish brown oily product.

Specific optical rotation $[\alpha]_D^{23}-11.0°$ (C=0.5, MeOH).

WORKING EXAMPLE 68
(S,S)-2-[3-t-Butoxycarbonylmethyl-2-oxopiperazine-1-yl]-2-methyl acetic acid t-butyl ester oxalate N-(2,2-Diethoxyethyl)-L-alanine t-butyl ester obtained in Working Example 67 was processed in substantially the same procedure as in Working Example 53 to afford the title compound as colorless prisms, m.p.175°–177° C. (decomp.).

Specific optical rotation $[\alpha]_D^{20}-34.4°$ (C=0.45, MeOH).
Elemental Analysis for $C_{17}H_{30}N_2O_5.C_2H_2O_4$:
Calcd.: C, 52.77; H, 7.46; N, 6.48.
Found: C, 52.67; H, 7.54; N, 6.61.

WORKING EXAMPLE 69
(S,S)-2-[4-(4-Amidinobenzoyl)glycyl-3-carboxymethyl-2-oxopiperazine-1-yl]-2-methyl acetic acid hydrochloride (S,S)-2-[3-t-Butoxycarbonylmethyl-2-oxopiperazine-1-yl]-2-methyl acetic acid t-butyl ester oxalate obtained in Working Example 68 was processed in substantially the same procedure as in Working Example 54 to afford the title compound as colorless powder.

Specific optical rotation $[\alpha]_D^{20}+52.7°$ (C=1.0, $H_2O$).
Elemental Analysis for $C_{19}H_{23}N_5O_7.HCl.H_2O$:
Calcd.: C, 46.77; H, 5 37; N, 14.35.
Found: C, 46.91; H, 5.43; N, 14.14.

WORKING EXAMPLE 70
(S)-3-N-(4,4,-Dimethoxybenzhydryl)carbamoylmethyl-2-oxo-piperazine-1-acetic acid t-butyl ester oxalate N-(2,2-Diethoxyethyl)glycine t-butyl ester was condensed with N($\alpha$)-carbobenzoxy-N($\beta$)-(4,4'-dimethoxybenzhydryl)-L-asparagine in substantially the same manner as in Working Example 2. The condensate was subjected to ring-closure and reduction in substantially the same manner as in Working Example 3 to afford the title compound, which was recrystallized from ethanol-ethyl ether to give colorless crystals, m p.120°–123° C.

Specific optical rotation $[\alpha]_D^{20}-5.1°$ (C=0.905, MeOH).

Elemental Analysis for $C_{27}H_{35}N_3O_6.C_2H_2O_4$:
Calcd.: C, 59.28; H, 6.35; N, 7.15.
Found: C, 59.01; H, 6.40; N, 7.06.

WORKING EXAMPLE 71
(S)-4-(4-Amidinobenzoyl)glycyl-3-carbamoylmethyl-2-oxopiperazine-1-acetic acid (S)-3-N-(4,4-Dimethoxybenzhydryl)carbamoylmethyl-2-oxopiperazine-1-acetic acid oxalate was processed in substantially the same manner as in Working Example 54 to give colorless powder, which was recrystallized from 50% methanol to afford the title compound as colorless crystals, m.p.226°–228° C.

Specific optical rotation $[\alpha]_D^{20}+70.3°$ (C=0.4, $H_2O$).
Elemental Analysis for $C_{18}H_{22}N_6O_6.2H_2O$:
Calcd.: C, 47.57; H, 5.77; N, 18.49.
Found: C, 47.35; H, 5.64; N, 18.28.

WORKING EXAMPLE 72
(S)-2-Benzyl-1-t-butoxycarbonyl-4-cyanomethyl-1,2,3,4-tetrahydropyrazine-3-one To a mixture of 3.0 g of 2,2-diethoxyethylaminoacetonitrile, 4.85 g of N-t-butoxycarbonyl-L-phenylalanine and 50 ml of methylene chloride was added 3.6 g of 1-ethyl-3-(3-dimethylaminopropyl)carbodiimide hydrochloride, which was stirred for 4 hours at room temperature. The reaction mixture was concentrated under reduced pressure. To the concentrate were added 100 ml of ethyl acetate and 50 ml of water. The mixture was shaken. The organic layer was separated, washed with water, dried over anhydrous magnesium sulfate and, then, concentrated under reduced pressure. The concentrate (7.0 g) was dissolved in 100 ml of ethyl acetate. To the solution was added 0.5 g of p-toluenesulfonic acid, and the mixture was stirred for 4 hours at 75° to 85° C. The reaction mixture was cooled and washed with an aqueous solution of sodium hydrogencarbonate, dried over anhydrous magnesium sulfate and concentrated under reduced pressure. The concentrate was purified by means of a silica-gel column chromatography (eluent: hexane—ethyl acetate=3:1), followed by recrystallization from ethyl acetate to afford 3.7 g of colorless prisms, m.p.160°-162° C.

Elemental Analysis for $C_{18}H_{21}N_3O_3$:
Calcd.: C, 66.04; H, 6.47; N, 12.84.
Found: C, 66.15; H, 6.57; N, 12.84.

WORKING EXAMPLE 73
(S)-3-Benzyl-1-(tetrazol-5-ylmethyl)-2-piperazinone hydrochloride A mixture of 1.0 g of (S)-2-benzyl-1-t-butoxycarbonyl-4-cyanomethyl-1,2,3,4-tetrahydropyrazin-3-one, 0.31 g of sodium azide, 0.25 g of ammonium chloride and 6 ml of N,N-dimethylformamide was stirred for 6 hours at 100° C. The reaction mixture was poured into ice-water, which was subjected to extraction with methylene chloride. The organic layer was washed with water and dried over anhydrous magnesium sulfate, then the solvent was distilled off under reduced pressure. To the solution of 1.0 g of the residue in 15 ml of ethanol was added 0.5 g of 10% palladium-carbon. The mixture was stirred for 20 hours in a hydrogen stream. The catalyst was filtered off, and the filtrate was concentrated under reduced pressure. To 1.0 g of the concentrate was added 8 ml of an ethyl acetate solution of 4N HCl, and the mixture was stirred for 3 hours at room temperature. Resulting precipitates were collected by filtration and recrystallized from methanol to afford 0.7 g of the title compound as colorless crystals, m.p.245°-247° C. (decomp.).

Specific optical rotation $[\alpha]_D^{20} - 105.7°$ (C=0.455, MeOH).

Elemental Analysis for $C_{13}H_{16}N_6O \cdot HCl \cdot 1/5H_2O$:
Calcd.: C, 49.97; H, 5.55; N, 26.92.
Found: C, 49.96; H, 5.60; N, 26.51.

WORKING EXAMPLE 74
(S)-3-Benzyl-4-glycyl-1-(tetrazol-5-ylmethyl)-2-piperazinone hydrochloride (S)-3-Benzyl-1-(tetrazol-5-ylmethyl)-2-piperazinone hydrochloride obtained in Working Example 73 (1.8 g) was subjected to substantially the same procedure as in Working Example 4 to afford 0.75 g of the title compound as colorless powder.

Specific optical rotation $[\alpha]_D^{20} + 59.1°$ (C=1.085, MeOH).

WORKING EXAMPLE 75
(S)-4-[4-(2-Aminoethylbenzoyl)glycyl]-3-benzyl-1-(tetrazol-5-ylmethyl)-2-piperazinone To a mixture of 0.2 g of (S)-3-benzyl-4-glycyl-1-(tetrazol-5-ylmethyl)-2-piperazinone hydrochloride, 0.16 g of 4-t-butoxycarbonylaminoethyl benzoic acid, 0.1 ml of triethylamine and 10 ml of methylene chloride was added 0.14 g of 1-ethyl-3-(3-dimethylaminopropyl)carbodiimide hydrochloride. The mixture was stirred for 20 hours at room temperature. The reaction mixture was washed with an aqueous solution of potassium hydrogensulfate, then with water, dried over anhydrous magnesium sulfate, followed by concentration under reduced pressure. The concentrate was dissolved in a mixture of 5 ml of ethyl acetate and 4 ml of methylene chloride. To the solution was added 4 ml of an ethyl acetate solution of 4N HCl, and the mixture was stirred for 24 hours at room temperature. Resulting precipitates were collected by filtration and purified by means of column chromatography on Amberlite XAD-2 (100 ml) (eluent:$H_2O$-methanol 4:1→4:3). The fraction thus obtained was freeze-dried to afford 0.20 g of the title compound as colorless powder.

Specific optical rotation $[\alpha]_D^{20} + 81.4°$ (C=0.46, MeOH).

Elemental Analysis for $C_{24}H_{28}N_8O_3 \cdot 3/2H_2O$:
Calcd.: C, 57.24; H, 6.21; N, 22.25.
Found: C, 56.99; H, 6.09; N, 22.49.

WORKING EXAMPLE 76
(S)-4-[4-(2-Aminoethyl)benzoyl]glycyl-1-carboxymethyl-2-oxopiperazine-3-propionic acid hydrochloride A mixture of 490 mg of (S)-1-benzyloxycarbonylmethyl-4-glycyl-2-oxopiperazine-3-propionic acid benzyl ester hydrochloride obtained in Working Example 31 and 290 mg of 4-(2-N-benzyloxycarbonylaminoethyl)benzoic acid was subjected to substantially the same procedure as in Working Example 32 to afford 240 mg of the title compound as amorphous powder.

Specific optical rotation: $[\alpha]_D^{25} + 62.7°$ (C=0.26, $H_2O$)

Elemental Analysis for $C_{20}H_{26}N_4O_7 \cdot HCl$:
Calcd.: C, 51.01; H, 5.78; N, 11.90.
Found: C, 51.29; H, 6.15; N, 11.81.

WORKING EXAMPLE 77
(S)-4-[4-(2-N,N-Dimethylaminoethyl)benzoyl]glycyl-1-carboxymethyl-2-oxopiperazine-3-propionic acid hydrochloride A mixture of 490 mg of (S)-1-benzyloxycarbonylmethyl-4-glycyl-2-oxopiperazine-3-propionic acid benzylester hydrochloride obtained in Working Example 31 and 230 mg of 4-(2-N,N-dimethylaminoethyl)benzoic acid hydrochloride was subjected to substantially the same procedure as in Working Example 32 to afford 310 mg of the title compound as amorphous powder.

Specific optical rotation: $[\alpha]_D^{25} + 61.5°$ (C=0.24, $H_2O$)

Elemental Analysis for $C_{22}H_{30}N_4O_7 \cdot HCl$:
Calcd.: C, 52.96; H, 6.26; N, 11.23.
Found: C, 52.93; H, 6.84; N, 11.34.

WORKING EXAMPLE 78
(S)-4-[(trans-4-Aminomethylcyclohexan)-1-ylcarbonyl]glycyl-1-carboxymethyl-2-oxopiperazine-3-propionic acid hydrochloride A mixture of 490 mg of (S)-1-benzyloxycarbonylmethyl-4-glycyl-2-oxopiperazine-3-propionic acid benzylester hydrochloride obtained in Working Example 31 and 290 mg of trans-4-(N-benzyloxycarbonylaminomethyl)cyclohexane carboxylic acid was subjected to substantially the same procedure as in Working Example 32 to afford 230 mg of the title compound as amorphous powder.

Specific optical rotation: $[\alpha]_D^{25} + 70.1$ (C=0.31, $H_2O$)

Elemental Analysis for $C_{18}H_{30}N_4O_7 \cdot HCl \cdot \frac{1}{2}H_2O$:
Calcd.: C, 48.36; H, 6.83; N, 11.87.
Found: C, 48.48; H, 6.73; N, 11.58.

WORKING EXAMPLE 79
(S)-4-(N-Benzyloxycarbonyl)glycyl-1-tert-butoxycarbonyl methyl-2-oxopiperazine-3-propionic acid methylester N-Benzyloxycarbonyl-L-glutamic acid-γ-methylester was subjected to substantially the same procedure as in Working Example 58 to afford the title compound as a colorless oily product.

Specific optical rotation: $[\alpha]_D^{25}+60.9°$ (C=1.3, MeOH)

WORKING EXAMPLE 80
(S)-4-[4-(2-Aminoethyl)benzoyl]glycyl-3-methoxycarbonyl ethyl-2-oxopiperazine-1-acetic acid hydrochloride By subjecting 490 mg of (S)-4-(N-benzyloxycarbonyl) glycyl-1-tert-butoxycarbonylmethyl-2-oxopiperazine-3-propionic acid methylester obtained in Working Example 79 and 270 mg of 4-(N-tert-butoxycarbonylaminoethyl)benzoic acid to substantially the same procedure as in Working Example 60, 270 mg of the title compound was obtained as amorphous powder.

Specific optical rotation: $[\alpha]_D^{25}+57.8°$ (C=0.26, H$_2$O)

Elemental Analysis for $C_{21}H_{36}H_4O_7 \cdot HCl$:
Calcd.: C, 52.01; H, 6.03; N, 11.55.
Found: C, 52.21; H, 6.26; N, 11.71.

WORKING EXAMPLE 81
(S)-4-[4-(2-N,N-Dimethylaminoethyl)benzoyl]glycyl-3-methoxycarbonylethyl-2-oxopiperazine-1-acetic acid hydrochloride By subjecting 490 mg of (S)-4-(N-benzyloxycarbonyl)glycyl-1-tert-butoxycarbonylmethyl-2-oxopiperazine-3-propionic acid methylester obtained in Working Example 79 and 230 mg of 4-(2-N,N-dimethylaminoethyl)benzoic acid to substantially the same procedure as in Working Example 60, 220 mg of the title compound was produced as amorphous powder.

Specific optical rotation: $[\alpha]_D^{25}+55.7°$ (C=0.29, H$_2$O)

Elemental Analysis for $C_{23}H_{32}N_4O_7 \cdot \frac{1}{2}HCl$:
Calcd.: C, 55.84; H, 6.62; N, 11.32.
Found: C, 55.81; H, 7.16; N, 11.21.

WORKING EXAMPLE 82
(S)-4-(trans-4-Aminomethylcyclohexan-1-ylcarbonyl)glycyl-3-methoxycarbonylethyl-2-oxopiperazine-1-acetic acid hydrochloride By subjecting 490 mg of (S)-4-(N-benzyloxycarbonyl) glycyl-1-tert-butoxycarbonylmethyl-2-oxopiperazine-3-propionic acid methylester obtained in Working Example 79 and 260 mg of trans-4-(N-tert-butoxycarbonylaminomethyl)cyclohexane carboxylic acid to substantially the same procedure as in Working Example 60, 190 mg of the title compound was produced as amorphous powder.

Specific optical rotation: $[60]_D^{25}+67.5°$ (C=0.36, H$_2$O)

Elemental Analysis for $C_{20}H_{32}N_4O_7 \cdot \frac{1}{2}HCl$:
Calcd.: C, 52.37; H, 7.14; N, 12.21.
Found: C, 52.41; H, 7.22; N, 12.09.

WORKING EXAMPLE 83
(S)-4-(N-Benzyloxycarbonyl)glycyl-3-N-(4,4-dimethoxybenz-hydryl)carbamoylethyl-2-oxopiperazine-1-acetic acid tbutyl ester (2,2-diethoxyethyl)glycine tbutylester and N-(α)-carbobenzoxy-N(γ)-(4,4'-dimethoxybenzhydryl)-L-glutamine were subjected to substantially the same procedure as in Working Example 58 and the reaction product was recrystallization from ethyl acetate to afford the title compound as colorless prisms, m.p. 98° C.

Specific optical rotation: $[\alpha]_D^{25}+39.4°$ (C=1.5, MeOH)

Elemental Analysis for $C_{38}H_{46}N_4O_9 \cdot \frac{1}{2}H_2O$:
Calcd.: C, 64.12; H, 6.66; N, 7.87.
Found: C, 64.08; H, 6.75; N, 8.23.

WORKING EXAMPLE 84
(S)-4-[4-(2-Aminoethyl)benzoyl]glycyl-3-carbamoylethyl-2-oxopiperazine-1-acetic acid hydrochloride By subjecting 700 mg of (S)-4-(N-benzyloxycarbonyl)glycyl-3-N-(4,4,-dimethoxybenzhydryl)carbamoylethyl-2-oxopiperazine-1-acetic acid tbutylester obtained in Working Example 83 and 265 mg of 4-(N-tert-butyloxycarbonylaminoethyl)benzoic acid to substantially the same procedure as in Working Example 60, 250 mg of the title compound was produced as amorphous powder.

Specific optical rotation: $[\alpha]_D^{25}+61.3°$ (C=0.27, H$_2$O)

Elemental Analysis for $C_{20}H_{27}N_5O_5 \cdot HCl \cdot H_2O$:
Calcd.: C, 49.23; H, 6.20; N, 14.35.
Found: C, 49.38; H, 6.16; N, 14.73.

WORKING EXAMPLE 85
(S)-4'-[4-(2-N,N-Dimethylaminoethyl)benzoyl]glycyl-3-carbamoylethyl-2-oxopiperazine-1-acetic acid hydrochloride By subjecting 700 mg of (S)-4-(Nbenzyloxycarbonyl) glycyl-3-N-(4,4'-dimethoxybenzhyiryl)carbamoylethyl-2-oxopiperazine-1-acetic acid tbutylester obtained in Working Example 83 and 230 mg of 4-(2-N,N-dimethylamino ethyl)benzoic acid to substantially the same procedure as in Working Example 60, 270 mg of the title compound was produced as amorphous powder.

Specific optical rotation: $[\alpha]_D^{25}+54.2°$ (C=0.40, H$_2$O)

Elemental Analysis for $C_{22}H_{31}N_5O_6 \cdot HCl$:
Calcd.: C, 53.06; H, 6.48; N, 14.06.
Found: C, 53.28; H, 6.76; N, 13.69.

WORKING EXAMPLE 86
(S)-4-(trans-4-Aminomethylcyclohexan-1-ylcarbonyl)glycyl-3-carbamoylethyl-2-oxopiperazine-1-acetic acid hydrochloride By subjecting 700 mg of (S)-4-(N-benzyloxycarbonyl)glycyl-3-N-(4,4'-dimethoxybenzhydryl)carbamoylethyl-2-oxopiperazine-1-acetic acid tbutylester obtained in Working Example 83 and 260 mg of trans-4-aminomethyl cyclohexane carboxylic acid to substantially the same procedure as in Working Example 60, 190 mg of the title compound as amorphous powder.

Specific optical rotation: $[\alpha]_D^{25}+62.6°$ (C=0.43, H$_2$O)

Elemental Analysis for $C_{19}H_{31}N_5O_6 \cdot HCl \cdot 2H_2O$:
Calcd.: C, 45.83; H, 7.29; N, 14.06.
Found: C, 46.05; H, 6.98; N, 14.03.

WORKING EXAMPLE 87
4-(2-Aminoethylbenzoyl)glycyl-2-oxopiperazine-1-acetic acid hydrochloride 4-Glycyl-2-oxopiperazine-1-acetic acid benzylester and 4-(2-N-benzyloxycarbonylaminoethyl)benzoic acid were subjected to substantially the same procedure as in Working Example 32 to afford the title compound.

Elemental Analysis for $C_{17}H_{22}N_4O_5 \cdot HCl$:
Calcd.: C, 51.19; H, 5.81; N, 14.05.
Found: C, 51.33; H, 5.91; N, 13.60.

WORKING EXAMPLE 88
(S)-4-[4-(2-Aminoethyl)benzoyl]glycyl-3-carbamoylmethyl-2-oxopiperazine-1-acetic acid hydrochloride (S)-3-N-(4,4,-Dimethoxybenzhydryl)carbamoylmethyl-2-oxopiperazine-1-acetic acid tbutylester oxalate obtained in Working Example 70 and 4-(2-tert-butoxycarbonylaminoethyl)benzoic acid were subjected to substantially the same procedure as in Working Example 60 to afford the title compound.

Specific optical rotation: $[\alpha]_D^{25} + 69.4°$ (C=0.775, H$_2$O)

Elemental Analysis for $C_{19}H_{25}N_5O_6 \cdot HCl \cdot 2H_2O$:
Calcd.: C, 46.39; H, 6.15; N, 14.24.
Found: C, 46.54; H, 5.88; N, 13.91.

WORKING EXAMPLE 89
(S)-4-[4-(2-Aminoethyl)benzoyl]glycyl-3-benzyl-2-oxopiperazine-1-acetic acid By subjecting (S)-3-benzyl-4-glycyl-2-oxopiperazine-1-acetic acid tert-butylester hydrochloride obtained in Working Example 15 and 4-(2-tert-butoxy carbonylaminoethyl)benzoic acid to substantially the same procedure as in Working Example 60, the title compound was produced.

Specific optical rotation: $[\alpha]_D^{20} + 93.7°$ (C=0.375, MeOH)

Elemental Analysis for $C_{24}H_{28}N_4O_5 \cdot 2.5H_2O$:
Calcd.: C, 57.94; H, 6.69; N, 11.26.
Found: C, 57.58; H, 6.40; N, 11.06.

EXAMPLES OF FORMULATION

In the case of using the compound (I) of this invention as a therapeutic agent for thrombosis, use is made of, for example, the following prescriptions.

1. Tablets

| | | |
|---|---|---|
| (1) | (S)-4-(4-amidinobenzoylglycyl)-2-oxopiperazine-1,3-diacetate | 10 g |
| (2) | lactose | 90 g |
| (3) | corn starch | 29 g |
| (4) | magnesium stearate | 1 g |
| | | 130 g |

The whole amounts of (1) and (2) are mixed with 17 g of (3) and the mixture is granulated with a paste prepared from 7 g of (3). With the granules are mixed g of (3) and the whole amount of (4). The whole mixture is subjected to compression-molding on a compression tableting machine to give 1000 tablets 7 mm in diameter and each containing 10 mg of (1).

2. Injectable solution

| | | |
|---|---|---|
| (1) | (S)-4-(4-amidinobenzoylglycyl)-2-oxopiperzine-1,3-diacetate | 10 g |
| (2) | sodium chloride | 9 g |

The whole amounts of (1) and (2) are dissolved in 1000 ml of distilled water. One ml each of the solution is put in 1000 brown ampoules. Air in the ampoules is replaced with nitrogen gas, and the ampoules are sealed. The whole procedure is conducted under sterilized conditions.

3. Tablets

| | | |
|---|---|---|
| (1) | (S)-4-(4-amidinobenzoylglycyl)-1-carboxymethyl-2-oxopiperazine-3-propionic acid | 10 g |
| (2) | lactose | 90 g |
| (3) | corn starch | 29 g |
| (4) | magnesium stearate | 1 g |
| | | 130 g |

The whole amounts of (1) and (2) are mixed with 17 g of (3) and the mixture is granulated with a paste prepared from 7 g of (3). With the granules are mixed 5 g of (3) and the whole amount of (4). The whole mixture is subjected to compression-molding on a compression tableting machine to give 1000 tablets 7 mm diameter and each containing 10 mg of (1).

4. Injectable solution

| | | |
|---|---|---|
| (1) | (S)-4-(4-amidinobenzoylglycyl)-1-carboxylmethyl-2-oxopiperazine-3-propionic acid | 10 g |
| (2) | sodium chloride | 9 g |

The whole amounts of (1) and (2) are dissolved in 1000 ml of distilled water. One ml each the solution is put in 1000 brown ampoules. The air in the ampoules is replaced with nitrogen gas, then the ampoules are sealed. The whole process is conducted under sterilized conditions.

The present invention is to provide novel compounds and pharmaceuticals effective for prophylaxis and therapy of various diseases by controlling or inhibiting cell adhesion.

We claim:

1. A compound represented by the formula $$G-D-\underset{O}{\overset{\Vert}{C}}-\underset{R^1}{\overset{|}{N}}-\underset{H}{\overset{|}{C}}-\underset{R^2}{\overset{|}{C}}-\underset{O}{\overset{\Vert}{C}}-N\underset{X\diagdown\diagup O}{\diagup\diagdown}N-\underset{R^3}{\overset{|}{C}}H-Z$$

wherein G is an amidino group or an optionally cyclic amino group each of which may be substituted; D is a spacer having 2 to 6 atomic chain optionally bonded through a hetero-atom and/or a 5- to 6-membered ring provided that the 5- to 6-membered ring is, depending on its bonding position, counted as 2 to 3 atomic chains; R$^1$ is hydrogen, benzyl group or a lower alkyl group; R$^2$ and R$^3$ are independently a residual group formed by removing —CH(NH$_2$)COOH from an α-amino acid, or R$^1$ and R$^2$ may form a 5- to 6-membered ring taken together with the adjacent N and C; X is hydrogen or an optionally substituted lower alkyl group; and Z is a group capable of forming an anion or a group convertible into an anion in a living body, or a physiologically acceptable salt thereof.

2. A compound of the formula

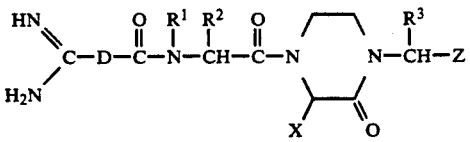

wherein D is a spacer having a 3 to 6 atomic chain optionally bonded through a hetero-atom and/or a 5- to 6-membered ring provided that the 5- to 6-membered ring is, depending on its bonding position, counted as 2 to 3 atomic chain; $R^1$ is hydrogen, benzyl group or a lower alkyl group; $R^2$ and $R^3$ are independently a residual group formed by removing —CH(NH$_2$)COOH from an α-amino acid; X is hydrogen or a lower alkyl group optionally substituted with a substituent selected from the group consisting of (1) optionally esterified or amidated carboxyl groups, (2) optionally substituted phenyl groups and (3) hydroxyl group; and Z is an salt thereof.

3. A compound as claimed in claim 1, wherein G is NH$_2$—.

4. A compound as claimed in claim 1, wherein G is the group of the formula

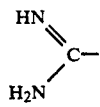

5. A compound as claimed in claim 1, wherein D is a group represented by the formula

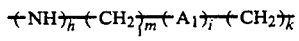

wherein h and i independently denote 0 or 1; m and k independently denote 0, 1 or 2; and $A_1$ stands for a 5- to 6-membered ring.

6. A compound as claimed in claim 5, wherein k=0.

7. A compound as claimed in claim 5, wherein k=0 and $A_1$ is benzene ring.

8. A compound as claimed in claim 5, wherein k=0 and $A_1$ is cyclohexane ring.

9. A compound as claimed in claim 5, wherein h=0, k=0 and $A_1$ is benzene ring.

10. A compound as claimed in claim 1, wherein X is benzyl group.

11. A compound as claimed in claim 1, wherein X is —CH$_2$COOH or —CH$_2$CH$_2$COOH.

12. A compound claimed in claim 1, wherein X is —CH$_2$COOCH$_3$ or —CH$_2$CH$_2$COOCH$_3$.

13. A compound claimed in claim 1, wherein X is —CH$_2$CONH$_2$ or —CH$_2$CH$_2$CONH$_2$.

14. A compound claimed in claim 1, wherein each of $R^1$, $R^2$ and $R^3$ is hydrogen atom..

15. A compound claimed in claim 1, wherein Z is —COOH.

16. The compound as claimed in claim 1, which is (S)-4-(4-amidinobenzoylglycyl)-2-oxopiperazine-1,3-diacetic acid or its hydrochloride.

17. The compound as claimed in claim 1, which is (S)-4-(4-amidinobenzoylglycyl)-1-carboxymethyl-2-oxopiperazine-3-propionic acid or its hydrochloride.

18. The compound as claimed in claim 1, which is (S)-4-[4-(2-aminoethyl)benzoylglycyl]-1-carboxymethyl-2-oxopiperazine-3-propionic acid or its hydrochloride.

19. The compound as claimed in claim 1, which is (S)-4-[4-(2-aminoethyl)benzoylglycyl]-1-carboxymethyl-2-oxopiperazine-1-acetic acid or its hydrochloride.

20. The compound as claimed in claim 1, which is (S)-4-[4-(2-aminoethyl)benzoylglycyl]-3-carbamoylmethyl-2-oxopiperazine-1-acetic acid or its hydrochloride.

21. The compound as claimed in claim 1, which is (S)-4-[4-(2-aminoethyl)benzoylglycyl]-3-methoxycarbonylmethyl-2-oxopiperazine-1-acetic acid or its hydrochloride.

22. The compound as claimed in claim 1, which is (S)-4-[4-(2-aminoethyl)benzoylglycyl]-3-methoxycarbonylmethyl-2-oxopiperazine-1-acetic acid or its hydrochloride.

23. The compound as claimed in claim 1, which is (S)-4-[4-(2-aminoethyl)benzoylglycyl]-3-carbamoylethyl-2-oxopiperazine-1-acetic acid or its hydrochloride.

24. A compound as claimed in claim 1, which is (S)-4-(4-Amidinobenzoylglycyl)-3-methoxycarbonylmethyl-2-oxopiperazine-1-acetic acid or its hydrochloride.

25. An agent for inhibiting cell-adhesion, which is characterized by containing the compound claimed in claim 1.

* * * * *